United States Patent
Yahata

(10) Patent No.: US 11,727,465 B2
(45) Date of Patent: Aug. 15, 2023

(54) METHOD FOR PROVIDING INFORMATION

(71) Applicant: Panasonic Intellectual Property Management Co., Ltd., Osaka (JP)

(72) Inventor: Hiroshi Yahata, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 17/485,570

(22) Filed: Sep. 27, 2021

(65) Prior Publication Data
US 2022/0012802 A1 Jan. 13, 2022

Related U.S. Application Data

(63) Continuation of application No. PCT/JP2020/010047, filed on Mar. 9, 2020.

(30) Foreign Application Priority Data

Feb. 10, 2020 (JP) ................................. 2020-020979

(51) Int. Cl.
G06Q 30/00 (2023.01)
G06Q 30/0601 (2023.01)
(Continued)

(52) U.S. Cl.
CPC ....... G06Q 30/0631 (2013.01); G06F 3/0482 (2013.01); G06F 16/9535 (2019.01);
(Continued)

(58) Field of Classification Search
CPC ........... G06Q 30/0631; G06Q 30/0201; G06Q 30/0282; G06Q 30/0639; G06Q 30/0641;
(Continued)

(56) References Cited

U.S. PATENT DOCUMENTS 8,429,026 B1 4/2013 Kolawa et al.
10,366,434 B1 7/2019 Belousova et al.
(Continued)

FOREIGN PATENT DOCUMENTS

CN 103246720 A 8/2013
CN 107679951 A 2/2018
(Continued)

OTHER PUBLICATIONS

Trevisiol, Michele, Luca Chiarandini, and Ricardo Baeza-Yates. "Buon appetito: recommending personalized menus." Proceedings of the 25th ACM conference on Hypertext and social media. (Year: 2014) (Year: 2014).*

(Continued)

*Primary Examiner* — Matthew E Zimmerman
(74) *Attorney, Agent, or Firm* — Greenblum & Bernstein, P.L.C.

(57) ABSTRACT

A method for providing information in an information management system that manages taste information regarding a user including an order record at a first restaurant and that associates the taste information with identification information for identifying the user. The method includes obtaining, from a terminal apparatus, the identification information and a store identifier indicating a second restaurant in a chain different from a chain to which the first restaurant belongs, arranging, on a basis of the taste information associated with the identification information and menu information regarding the second restaurant indicated by the store identifier, menu items included in the menu information in order according to the taste information, and transmitting menu information regarding the menu items arranged in the order to the terminal apparatus to display the menu information regarding the menu items arranged in the order on a display screen of the terminal apparatus.

16 Claims, 19 Drawing Sheets

(51) Int. Cl.
  *G06F 3/0482* (2013.01)
  *G06Q 30/0201* (2023.01)
  *G06F 16/9535* (2019.01)
  *G06Q 30/0282* (2023.01)
  *H04W 4/021* (2018.01)
  *G06F 21/32* (2013.01)
  *G16H 40/67* (2018.01)
  *H04L 9/40* (2022.01)

(52) U.S. Cl.
  CPC ......... *G06F 21/32* (2013.01); *G06Q 30/0201* (2013.01); *G06Q 30/0282* (2013.01); *G06Q 30/0639* (2013.01); *G06Q 30/0641* (2013.01); *G06Q 30/0643* (2013.01); *H04W 4/021* (2013.01); *G16H 40/67* (2018.01); *H04L 63/0861* (2013.01)

(58) Field of Classification Search
  CPC ............ G06Q 30/0643; G06F 16/9535; G06F 3/0482; G06F 21/32; H04W 4/021; G16H 40/67; H04L 63/0861
  See application file for complete search history.

(56) References Cited

U.S. PATENT DOCUMENTS

| | | |
|---|---|---|
| 2009/0048027 A1 | 2/2009 | Palmisano |
| 2010/0332271 A1 | 12/2010 | De Spong |
| 2013/0211959 A1 | 8/2013 | Marusyk et al. |
| 2013/0339163 A1* | 12/2013 | Dumontet .......... G06Q 30/0631 705/15 |
| 2014/0324607 A1 | 10/2014 | Frehn et al. |
| 2018/0032899 A1 | 2/2018 | Nguyen et al. |
| 2018/0308143 A1 | 10/2018 | Chan et al. |
| 2018/0308155 A1 | 10/2018 | Kohli et al. |
| 2020/0410496 A1 | 12/2020 | Margolin et al. |
| 2021/0035196 A1 | 2/2021 | Resheff et al. |
| 2021/0073768 A1* | 3/2021 | Gordon ................ G06Q 20/202 |
| 2021/0142226 A1 | 5/2021 | Sahni et al. |

FOREIGN PATENT DOCUMENTS

| | | | |
|---|---|---|---|
| CN | 109816469 A | | 5/2019 |
| JP | 2004295205 A | * | 10/2004 |
| JP | 2009-064348 | | 3/2009 |
| JP | 2009-245274 | | 10/2009 |
| JP | 2014-048875 | | 3/2014 |
| JP | 2014-52944 | | 3/2014 |
| JP | 2017-228040 | | 12/2017 |
| WO | WO-2007041672 A2 | * | 4/2007 ............. G06Q 30/02 |

OTHER PUBLICATIONS

International Search Report of PCT application No. PCT/JP2020/010047 dated Jul. 7, 2020.
Office Action issued in U.S. Appl. No. 17/485,591, dated Dec. 23, 2022.
Office Action issued in U.S. Appl. No. 17/485,594, dated Dec. 23, 2022.
English Translation of Chinese Search Report dated Apr. 29, 2023 for the related Chinese Patent Application No. 202080081216.9.

* cited by examiner

| ORDER TIME INFORMATION | STORE ID | STORE NAME | ORDERED ITEM NAMES |
|---|---|---|---|
| 2020-01-03T13:15:45.000Z | A1 | RESTAURANT CHAIN A KADOMA STORE | CAPPUCCINO, ICE CREAM |
| 2020-01-04T17:05:11.000Z | B1 | RESTAURANT CHAIN B MORIGUCHI STORE | BACON, EGG, AND CHEESE BURGER, OOLONG TEA |
| 2020-01-04T22:27:06.000Z | C1 | RESTAURANT CHAIN C MORISHOJI STORE | VONGOLE BIANCO, CAFFE MOCHA, ICE CREAM |
| 2020-01-05T09:23:31.000Z | D1 | RESTAURANT CHAIN D TSURUMIRYOKUCHI STORE | DAN DAN NOODLES & CHINESE DUMPLINGS SET |
| 2020-01-07T11:01:23.000Z | A2 | RESTAURANT CHAIN A KYOBASHI STORE | CAPPUCCINO |
| ·· | ·· | ·· | ·· |

| ITEM NAME | PRICE | TIME LIMIT |
|---|---|---|
| BLENDED COFFEE | 300 | No |
| AMERICAN COFFEE | 300 | No |
| CAFE AU LAIT | 350 | No |
| ESPRESSO | 300 | No |
| CAPPUCCINO | 350 | No |
| CAFFE MOCHA | 350 | No |
| CHOCOLATE COOKIE | 150 | No |
| SPECIAL MONT BLANC WHITE CAFFE LATTE | 600 | Yes |
| ⋮ | ⋮ | ⋮ |

FIG. 14

| ITEM NAME | TOTAL NUMBER OF ORDERS | NUMBER OF ORDERS AT SPECIFIED RESTAURANT CHAIN |
|---|---|---|
| BLENDED COFFEE | 0 | 0 |
| AMERICAN COFFEE | 0 | 0 |
| CAFE AU LAIT | 2 | 0 |
| ESPRESSO | 0 | 0 |
| CAPPUCCINO | 29 | 0 |
| CAFFE MOCHA | 11 | 0 |
| CHOCOLATE COOKIE | 3 | 0 |
| SPECIAL MONT BLANC WHITE CAFFE LATTE | 0 | 0 |
| ·· | ·· | ·· |

METHOD FOR PROVIDING INFORMATION

BACKGROUND

1. Technical Field

The present disclosure relates to a method for providing information in an information provision system.

2. Description of the Related Art

Japanese Unexamined Patent Application Publication No. 2009-64348 discloses an order system that obtains order records of a customer and that presents an order proposal relating to foods and drinks to the customer on the basis of information regarding the obtained order records in order to save the customer the trouble of finding foods and drinks that suit his/her taste on a menu at a restaurant.

SUMMARY

Further improvements are needed in the above example of the related art.

In one general aspect, the techniques disclosed here feature a method for providing information in an information management system that manages taste information regarding a user including an order record at a first restaurant and that associates the taste information with identification information for identifying the user. The method includes obtaining, from a terminal apparatus, the identification information and a store identifier indicating a second restaurant in a chain different from a chain to which the first restaurant belongs, the store identifier being selected on the terminal apparatus, arranging, on a basis of the taste information associated with the identification information and menu information regarding the second restaurant indicated by the store identifier, menu items included in the menu information in order according to the taste information, the menu information being obtained, over a network, from a server relating to the second restaurant indicated by the store identifier, and transmitting menu information regarding the menu items arranged in the order to the terminal apparatus to display the menu information regarding the menu items arranged in the order on a display screen of the terminal apparatus.

With the above aspect, further improvements can be achieved.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 12 is a diagram illustrating an example of the data configuration of an order record database storing order records;

FIG. 13 is a diagram illustrating an example of the data configuration of standard menu information;

FIG. 14 is a table illustrating the number of orders, placed by a certain user, for each of foods and drinks included in the standard menu information;

DETAILED DESCRIPTION

Figure 1:
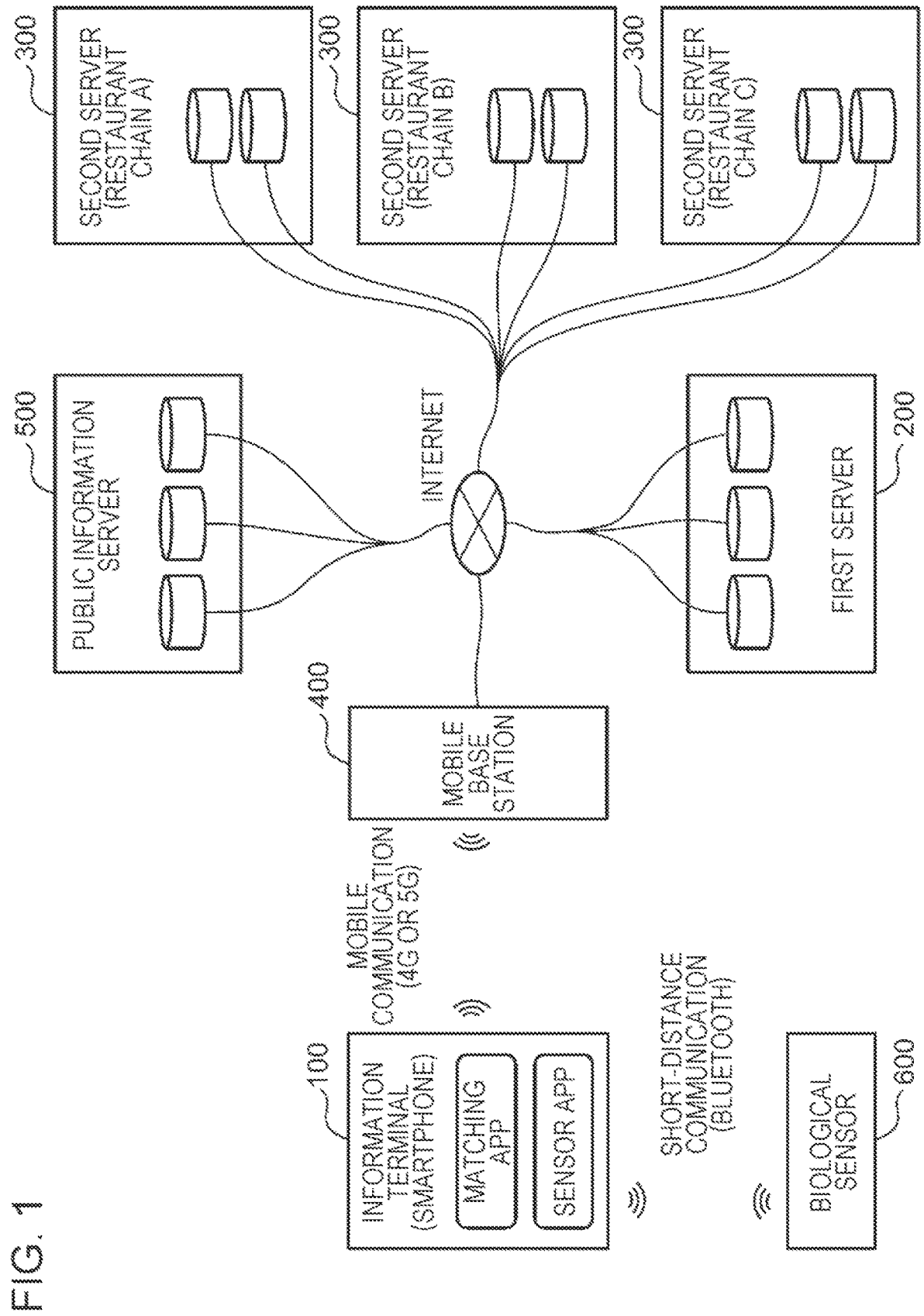
FIG. 1 is a diagram illustrating an example of the entirety of an information provision system in the present disclosure.

Underlying Knowledge Forming Basis of the Present Disclosure

Today, with development of a restaurant industry, various chain stores that serve foods and drinks, such as family restaurants, hamburger shops, coffee shops, and Chinese restaurants, are being deployed on a nationwide scale. Different stores often share the same menu table if the stores belong to the same chain. Even when the user is visiting a store for a first time, therefore, the user can efficiently order foods and drinks using a familiar menu table if the store belongs to a familiar chain.

If the user is visiting for a first time a store managed by a chain that the user has never used, however, the user needs to order foods and drinks using an unfamiliar menu table, which can be troublesome.

In the technique disclosed in Japanese Unexamined Patent Application Publication No. 2009-64348, information regarding order records of the user is obtained from an order record database, and an order proposal to be presented to the user is generated on the basis of the information regarding the order records. With the technique disclosed in this example of the related art, however, an order proposal is generated using only order records of the user at a store that the user is visiting. With the technique disclosed in this example of the related art, therefore, when the user is visiting a store for a first time, for example, it is difficult to generate an order proposal since there are no order records at the store. With the technique disclosed in this example of the related art, therefore, it is difficult to address the troublesomeness described above.

When it is difficult to generate an order proposal, a standard menu for general customers might be presented to the user's mobile terminal at a store. Because mobile terminals have limitations in display area, however, foods and drinks that the user is not interested in might be displayed at positions of high priority. In this case, the user needs to find desired foods and drinks through scrolling or the like, which can be troublesome.

One non-limiting and exemplary embodiment provides a technique for enabling the user to efficiently select foods and drinks that suit his/her taste using a terminal apparatus having a limitation in display area.

A method for providing information according to an aspect of the present disclosure is a method for providing information in an information management system that manages taste information regarding a user including an order record at a first restaurant and that associates the taste information with identification information for identifying the user. The method includes obtaining, from a terminal apparatus, the identification information and a store identifier indicating a second restaurant in a chain different from a chain to which the first restaurant belongs, the store identifier being selected on the terminal apparatus, arranging, on a basis of the taste information associated with the identification information and menu information regarding the second restaurant indicated by the store identifier, menu items included in the menu information in order according to the taste information, the menu information being obtained, over a network, from a server relating to the second restaurant indicated by the store identifier, and transmitting menu information regarding the menu items arranged in the order to the terminal apparatus to display the menu information regarding the menu items arranged in the order on a display screen of the terminal apparatus.

According to this aspect, the information management system manages taste information regarding a user including an order record at a first restaurant while associating the taste information with identification information for identifying the user. A store identifier indicating a second restaurant different from the first restaurant is selected on a terminal apparatus used by the user. As a result of the selection, menu items included in menu information regarding the second restaurant are arranged in order according to the taste information regarding the user, and menu information regarding the menu items arranged in the order is displayed on a display screen of the terminal apparatus.

Consequently, the user can display, at positions of high priority in the order according to the taste information, the menu items included in the menu information regarding the second restaurant on the display screen of the terminal apparatus that has a limitation in display area on the basis of the taste information including the order record at the first restaurant, which the user has used before, even if the user is using the second restaurant for a first time.

The user, therefore, can efficiently select foods and drinks that suit his/her taste even if the user is using the second restaurant for the first time, In the method, the second restaurant may include a coffee shop in a chain different from the chain to which the first restaurant belongs.

According to this aspect, at a coffee shop in a certain chain, menu information in which menu items are arranged in order according to taste information including an order record at a coffee shop in another chain is displayed. Even if the user is using a coffee shop in a certain chain for a first time, for example, therefore, the user can efficiently select foods and drinks that suit his/her taste.

In the method, the second restaurant may include a hamburger shop in a chain different from the chain to which the first restaurant belongs.

According to this aspect, at a hamburger shop in a certain chain, menu information in which menu items are arranged in order according to taste information including an order record at a hamburger shop in another chain is displayed. Even if the user is using a hamburger shop in a certain chain for a first time, therefore, the user can efficiently select foods and drinks that suit his/her taste.

The method may further include obtaining positional information regarding the terminal apparatus of the user and providing, on a basis of the positional information, the terminal apparatus with restaurant information indicating one or more restaurants in an area including a position indicated by the positional information. The store identifier may be selected on the terminal apparatus on a basis of the restaurant information.

According to this aspect, the user can select a desired restaurant among restaurants around a position thereof. Menu items included in menu information regarding the selected restaurant are then arranged in order according to taste information regarding the user. Even if the user is using the selected restaurant for a first time, the user can efficiently select foods and drinks that suit his/her taste.

The method may further include obtaining the positional information regarding the terminal apparatus of the user using a global positioning system.

According to this aspect, positional information regarding a terminal apparatus is obtained using a global positioning system. A position of the user, therefore, can be accurately detected, and restaurants around the user can be presented to the user.

In the method, if there is no order record of the user at the second restaurant in the information management system, the menu items included in the menu information regarding the second restaurant may be arranged in the order according to the taste information associated with the identification information on a basis of the taste information and the menu information regarding the second restaurant.

According to this aspect, if there is no order record of the user at the second restaurant, menu information based on taste information including an order record at the first restaurant is displayed. As a result, even if the user is using for a first time a chain to which the second restaurant belongs, the user can efficiently select foods and drinks that suit his/her taste.

In the method, if there is an order record of the user at the second restaurant in the information management system, the menu items included in the menu information regarding the second restaurant may be arranged in order according to the order record at the second restaurant on a basis of the order record at the second restaurant and the menu information regarding the second restaurant.

If the second restaurant is not a restaurant that the user uses for a first time, it might be more convenient for the user to generate menu information on the basis of an order record at the second restaurant, instead of taste information including an order record at the first restaurant. According to this aspect, if there is an order record of the user at the second restaurant, menu information in which menu items are arranged in order according to the taste information including the order record at the second restaurant is displayed. If the user has used the second restaurant before, therefore, the user can efficiently select foods and drinks that suit his/her taste using the menu information that reflects the order record at the second restaurant.

In the method, if a number of order records of the user at the second restaurant is smaller than a certain value in the information management system, the menu items included in the menu information regarding the second restaurant may be arranged in the order according to the taste information associated with the identification information on a basis of the taste information and the menu information regarding the second restaurant.

If the user is not using the second restaurant for a first time but has not used the second restaurant many times, menu information that sufficiently reflects the user's taste might not be generated when menu information is generated for the user on the basis of the order record at the second restaurant. According to this aspect, if the number of order records at the second restaurant is smaller than a certain value, menu information in which menu items are arranged on the basis of taste information including not only the order record at the second restaurant but also an order record at another restaurant is displayed. It is therefore possible to prevent menu information that does not sufficiently reflect the user's taste from being displayed at the second restaurant.

In the method, if the number of order records of the user at the second restaurant is larger than or equal to the certain value in the information management system, the menu items included in the menu information regarding the second restaurant may be arranged in order according to the order record at the second restaurant on a basis of the order record at the second restaurant and the menu information regarding the second restaurant.

If the user has used the second restaurant a certain number of times or more, it might be more convenient for the user to generate menu information on the basis of order records at the second restaurant, instead of taste information including an order record at the first restaurant. According to this aspect, if the number of order records at the second restaurant is larger than or equal to a certain value, menu information in which menu items are arranged on the basis of the order records at the second restaurant is displayed. If the user has used the second restaurant the certain number of times or more, therefore, the use can efficiently select foods and drinks that suit his/her taste using the menu information that reflects the order records at the second restaurant.

In the method, if a latest order record of the user at the second restaurant precedes a certain period of time in the information management system, the menu items included in the menu information regarding the second restaurant may be arranged in the order according to the taste information associated with the identification information on a basis of the taste information and the menu information regarding the second restaurant.

Even if the user is not using the second restaurant for a first time, the user's taste might have changed when, for example, the user has not used the second restaurant for a long time. In this case, menu information regarding the second restaurant might not be displayed desirably. According to this aspect, menu information that reflects taste information including an order record at the first restaurant is displayed in this case, and the user can efficiently select foods and drinks that suit his/her taste.

In the method, if the latest order record of the user at the second restaurant is within the certain period of time in the information management system, the menu items included in the menu information regarding the second restaurant may be arranged in order according to the order record at the second restaurant on a basis of the order record at the second restaurant and the menu information regarding the second restaurant.

If the user is not using the second restaurant for a first time and a last time that the user has used the second restaurant is not so long ago, it might be more convenient for the user to display menu information that reflects an order record at the second restaurant, instead of taste information based on an order record at the first restaurant. According to this aspect, since the menu information that reflects the order record at the second restaurant is displayed in this case, the user can efficiently select foods and drinks that suit his/her taste.

A method for providing information according to another aspect of the present disclosure is a method for providing information in an information management system that manages taste information regarding a user including an order record at a first restaurant and that associates the taste information with identification information for identifying the user. The method includes obtaining positional information regarding a terminal apparatus of the user, providing, on a basis of the positional information, the terminal apparatus with restaurant information indicating one or more restaurants in an area including a position indicated by the positional information, obtaining, from the terminal apparatus, the identification information and a store identifier indicating, among the one or more restaurants, a second restaurant in a chain different from a chain to which the first restaurant belongs, the store identifier being selected on the terminal apparatus, arranging, on a basis of the taste information associated with the identification information and menu information regarding the second restaurant indicated by the store identifier, menu items included in the menu information in order according to the taste information, the menu information being obtained, over a network, from a server relating to the second restaurant indicated by the store identifier, and transmitting menu information regarding the menu items arranged in the order to the terminal apparatus to display the menu information regarding the menu items arranged in the order on a display screen of the terminal apparatus.

According to this aspect, the information management system manages taste information regarding a user including an order record at the first restaurant while associating the taste information with identification information for identifying the user. Restaurant information indicating one or more restaurants in an area including a position indicated by positional information regarding a terminal apparatus of the user is provided on the basis of the positional information. As a result, a store identifier indicating a second restaurant in a chain different from a chain to which the first restaurant belongs is selected on the terminal apparatus among the one or more restaurants. As a result of this selection, menu items included in menu information regarding the second restaurant are arranged in order according to the taste information regarding the user, and menu information regarding the menu items arranged in the order is displayed on a display screen of the terminal apparatus.

Consequently, even if the user has never used the second restaurant, the menu items included in the menu information regarding the second restaurant can be displayed on the display screen of the terminal apparatus having a limitation in display area in a prioritized manner in the order according to the taste information on the basis of the taste information including the order record at the first restaurant, which the user has used before.

As a result, even if the user has never used the second restaurant, the user can efficiently check and select a menu that suits his/her taste.

The present disclosure can also be implemented as a program for causing a computer to achieve the characteristic components included in the method for providing information or an information provision system or a terminal apparatus that operates in accordance with the program. It is needless to say that such a computer program may be distributed using a non-transitory computer-readable recording medium such as a compact disc read-only memory (CD-ROM) or a communication network such as the Internet.

Embodiment

It is expected that the Internet will continue to spread in our society and various sensors will become more familiar to us. As a result, it is expected that information regarding persons' conditions and activities, as well as information regarding entire cities, including buildings and transportation networks, will be digitized and become available in computer systems. Digitized data regarding persons (personal information) will be accumulated in the cloud via communication networks, managed, as big data, by information banks that have a mechanism for enabling third parties to access the data with the person's permission, and used for various purposes for individuals and society.

Such a highly information-oriented society is called "Society 5.0" in Japan. The highly information-oriented society is a society where economic development and solutions to social issues are expected through an information infrastructure (cyber-physical system) that highly integrates real space (physical space) and virtual space (cyber space).

When a person makes decisions in such a highly information-oriented society in various daily situations, the person can analyze the big data including the accumulated personal information and identify possible optimal options therefor according to the situation at the time.

In the following description, modes for achieving economic efficiency and personalization in a highly information-oriented society where such a cyber-physical system operates will be described with a theme of personal meals.

In Society 5.0, servers of business operators, which are called "information banks", singlehandedly manage personal information such as taste information indicating a user's taste by encrypting and concealing the personal information so that the personal information becomes inaccessible by third parties without the user's permission. Most of the personal information does not require the user's conscious input operation, and is continuously collected and updated from time to time under the management of the information banks.

An example of a personalized ordering system for foods and drinks transmits menu information from a restaurant server to a person's information terminal and presents a menu including foods and drinks that suit the user's taste on the information terminal as a recommended menu.

FIG. 1 is a diagram illustrating an example of the entirety of an information provision system in the present disclosure. The information provision system illustrated in FIG. 1 is a system configured on the basis of Society 5.0 and provides a user, who is a consumer whose personal information is used, with a selection support service for supporting selection of a product or a service by presenting products or services suitable for the user. In a first embodiment, a service that supports ordering of foods and drinks will be described as the selection support service. More specifically, the information provision system presents an optimal menu to a user by matching menu information viewed by the user to order foods and drinks when eating out with personal information regarding the user.

The information provision system includes three apparatus groups. A first apparatus group includes an information terminal 100 (an example of a terminal apparatus) owned by the user, such as a smartphone. A matching application is installed on the information terminal 100. The matching application (hereinafter referred to as a "matching app") selects or recommends products or services suitable for a user using personal information regarding the user. Personal information herein broadly includes public or non-public information regarding a person. For example, personal information includes a name, a date of birth, an address, annual income, movables and immovables, physical information such as height and weight, genetic information, allergy information, medical information such as medical history and diagnosis charts, activity information such as the number of steps and calories burned, meal record information, vital sign information such as heartbeat and blood pressure, purchase information via stores and electronic commerce (EC) websites, word information regarding words used in searches using web search engines and artificial intelligence (AI) speakers, information regarding text and images sent and received by mail and social networking services (SNSs), movement record information, and/or the like. The information terminal 100 can be connected to the Internet via a mobile base station 400 by, for example, a mobile communication network called "4G" or "5G".

A second apparatus group includes a first server 200.

The first server 200 is a personal information server that stores personal information regarding the user while splitting the personal information between different locations and encrypting the split personal information. For example, the first server 200 manages the personal information regarding the user by storing the personal information in different storage devices on the cloud while fragmenting and encrypting the personal information. As a result, high security is ensured, and leakage of the personal information is prevented. The first server 200 also has a function of returning necessary data in response to an inquiry from a third party with the user's permission. Furthermore, the first server 200 has a function of securely sharing personal information selected by the user to a business operator authorized by the user. That is, the first server 200 has a function as an information bank. In this case, for example, the first server 200 stores a piece of data while splitting the piece of data between different storage devices. An example of the piece of data is a file containing personal information.

In the present embodiment, the first server 200 causes a specific business operator to share specific personal information with the user's permission. The first server 200 also has a function for providing the selection support service, which will be described later.

The matching app described above is developed and/or distributed by, for example, a company that manages the first server 200. The company evaluates, using personal information regarding the user, a degree of suitability of the user to products or services that might be used by the user. The company that manages the first server 200, a company that develops the matching app, and a company that distributes the matching app may be the same or different from one another. The information provision system illustrated in FIG. 1 achieves the selection support service using the above-described matching app, but this is just an example. For example, the selection support service may be achieved using an application other than the matching app, a common browser, or the like, instead. In order to handle the personal information regarding the user securely, it is preferable to provide the selection support service using a dedicated application such as the matching app. This, however, is just an example, and when personal information whose degree of security importance is low, such as publicly available personal information, is handled, or when a function for ensuring security, such as hypertext transfer protocol secure (HTTPS) communication, is provided using an Internet browser, the selection support service may be provided by means other than the matching application.

The matching app handles personal information only inside the information terminal 100. The matching app presents the user with products or services that are estimated to be most suitable for the user under conditions such as a time, a place, and a situation. For example, the matching app provides a mediation function in economic activities such as purchase by the user.

The matching app opens up a recommendation function, which has been isolated to each service provider. For example, an example of a service provider famous in an EC market such as EC websites will be described. A large number of products are listed on the service provider's website. When a user searches for or purchases a particular product, other products that are highly relevant to that product (e.g., products that are often purchased together) are recommended to the user. The recommendation function for such purchase is effective only on the EC website of the service provider. The recommendation function, therefore, has no effect when the user purchases products on EC websites operated by other service providers, when the user orders meals at restaurants, or when the user plans family vacations.

It is expected in the future that personal information will be aggregated in information banks and a mechanism will be established in which anyone can access, under certain conditions, an enormous amount of a wide variety of accurate personal information obtained over a long period of time. In this case, a degree of suitability can be estimated, on the basis of searches or purchase histories on an EC website of a service provider and personal information regarding various users, for not only a product of the service provider but also any product or service. This makes it possible to recommend products or services that are more valuable to a user from among various options.

The first server 200 assumed in the present embodiment is a cloud server that, in order to achieve the above idea or function, stores personal information in different storage devices while splitting and encrypting the personal information and manages and controls access to the personal information from the outside.

A third apparatus group includes second servers 300 in which business operators manage data unique thereto. Each of the business operators owns or rents one of the second servers 300 and manages and/or provides information regarding products and/or services thereof. In the present embodiment, the business operators are companies that operate chain stores. In the example illustrated in FIG. 1, three second servers 300 are operated by restaurant chains A to C, respectively. Restaurant chain A is, for example, chain stores managed by company A, restaurant chain B is, for example, chain stores managed by company B, and restaurant chain C is, for example, chain stores managed by company C. Chain stores refer to a management form in which a large number of stores are operated and managed with a brand, a management policy, services, appearance, and the like given a sense of unity. Restaurants deployed as chain stores include family restaurants, coffee shops, and hamburger shops. The business operators may be ready-to-eat meal companies where customers can take out cooked food, such as lunch vendors and fast-food restaurants. Alternatively, the business operators may be business operators that sell foodstuffs for home cooking, such as supermarkets. The second servers 300 are, for example, cloud servers.

Although different companies manage restaurant chains A to C in the example illustrated in FIG. 1, this is just an example. The same company may manage restaurant chains A to C, instead. In addition, although there are three second servers 300 in the example illustrated in FIG. 1, this is just an example. There may be one, two, or four or more second servers 300, instead.

One of advantageous effects produced by the information provision system according to the present embodiment is that personal information is not given to business operators without the user's permission. This is because the first server 200, which has the function of an information bank, is configured to share specific pieces of information to only specific business operators with the user's permission.

It is troublesome, however, to let each of users determine how to operate personal information regarding the user. Even if there is a trust company that sets a data operation policy, it is difficult for the users to understand which pieces of data have been given and who has received the pieces of information, which can make the users feel uneasy.

In the present embodiment, therefore, the business operator that operates the first server 200 may be inhibited or restricted from using, that is, decrypting and interpreting, for example, the stored personal information without the user's permission.

Furthermore, when an information bank or an information intermediary that manages personal information and provides the matching app enters a market under an operation policy strict about privacy, the user may make a contract with the information bank or the information intermediary in order to receive the service. This makes it possible to prevent personal information from being given to a business operator without the user's permission.

The information provision system according to the present embodiment is a mode of an operation system in a next-generation information society that reduces a possibility that personal information including sensitive information will be known to a third party and that can use, with personal permission, an enormous amount of personal information which changes from moment to moment for matching with various services. The information provision system will be described hereinafter on this assumption.

The information provision system illustrated in FIG. 1 further includes a biological sensor 600 and a public information server 500.

The public information server 500 manages public information different from information regarding restaurants and personal information. The public information server 500 is connected to the Internet. For example, the public information includes map information, weather information, and traffic information. These pieces of information are used if necessary for matching.

The biological sensor 600 is a smartwatch or the like. The biological sensor 600 is worn by the user who owns the information terminal 100. The biological sensor 600 continuously measures vital sign information and/or activity information regarding the user. The biological sensor 600 transmits the vital sign information and/or the activity information measured thereby to the information terminal 100 through short-distance communication such as Bluetooth (registered trademark). The vital sign information and/or the activity information are stored and/or managed by a sensor app installed on the information terminal 100. The sensor app uploads, to the first server 200 in accordance with user account information, the collected vital sign information and/or activity information and time information indicating times at which the vital sign information and/or the activity information have been measured. The vital sign information and/or the activity information are thus accumulated.

The sensor app may give rights to access the stored and/or managed data to the matching app or an operating system (OS) of the information terminal 100. In this case, the vital sign information and/or the activity information are uploaded to the first server 200 via the matching app or the OS. The sensor app may store the vital sign information and/or the activity information in a memory of the information terminal 100 or by uploading the vital sign information and/or the activity information to the first server 200.

Figure 2:
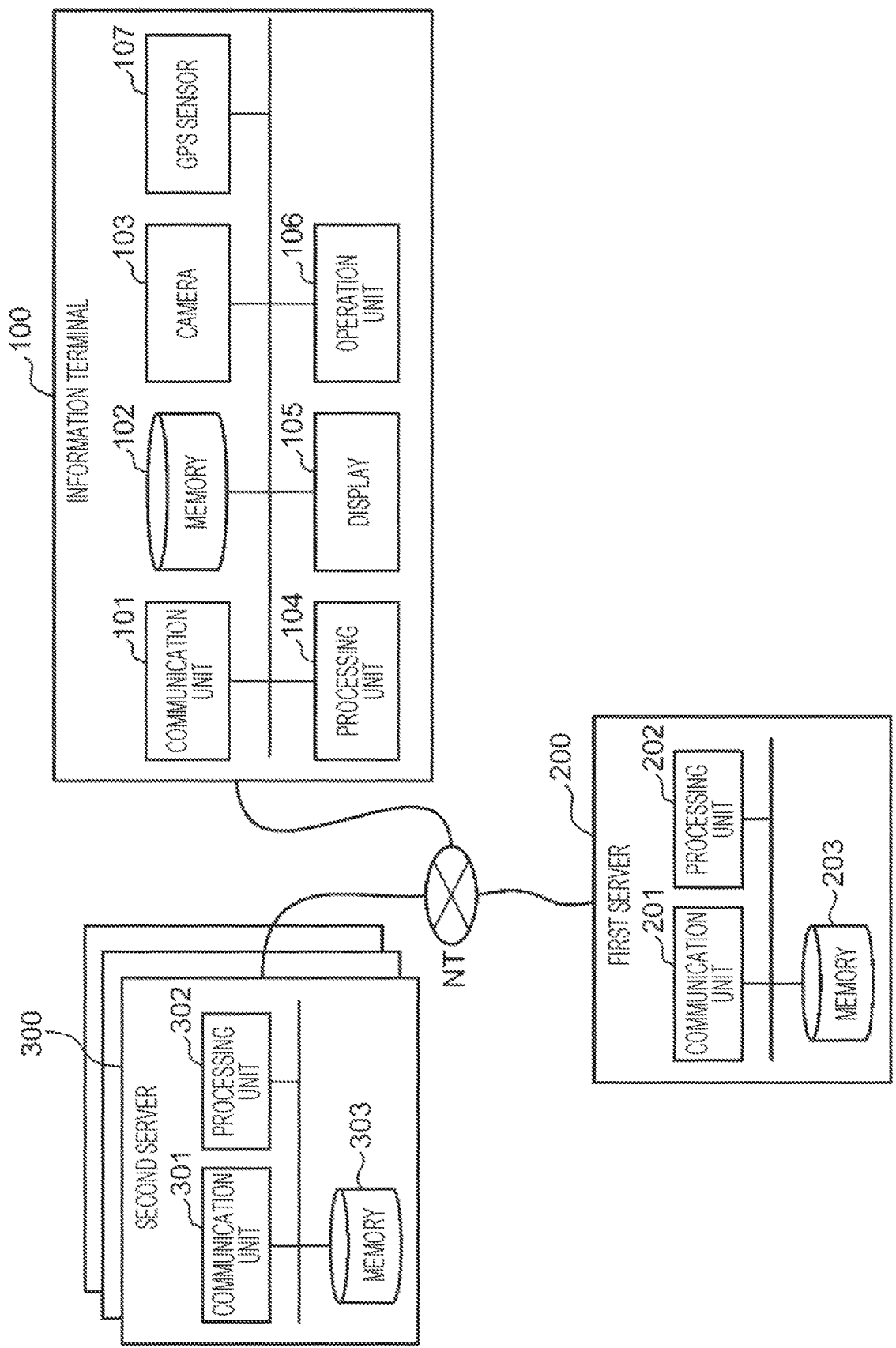
FIG. 2 is a diagram illustrating an example of a specific configuration of the information provision system according to a first embodiment.

FIG. 2 is a diagram illustrating an example of a specific configuration of the information provision system according to the present embodiment. The information provision system illustrated in FIG. 2 includes the information terminal 100, the first server 200, and the second servers 300 described with reference to FIG. 1. FIG. 2 does not illustrate the mobile base station 400 and the biological sensor 600 for convenience of description. The information terminal 100, the first server 200, and the second servers 300 are communicably connected to one another over a network NT. The network NT is a wide-area communication network including a mobile phone communication network and the Internet.

The information terminal 100 is achieved by a mobile information processing apparatus such as a smartphone or a tablet terminal. In the present embodiment, the information terminal 100 is carried by a user who orders foods and drinks at stores in restaurant chains. The information terminal 100 includes a communication unit 101, a memory 102, a camera 103, a processing unit 104, a display 105, an operation unit 106, and a global positioning system (GPS) sensor 107.

The communication unit 101 is achieved by a communication circuit that connects the information terminal 100 to the network NT. The communication unit 101 transmits, to the first server 200, a store identifier (ID) of a second restaurant in a chain different from one to which a first restaurant belongs while associating the store ID with identification information regarding the user, the first restaurant having been selected by the user using the operation unit 106. The first restaurant belongs to a restaurant chain that the user frequently uses. The second restaurant belongs to a restaurant chain different from the one to which the first restaurant belongs.

The communication unit 101 receives menu information, which will be described later, transmitted from one of the second servers 300. The processing unit 104 displays the menu information received by the communication unit 101 on the display 105. The communication unit 101 transmits, under the control of the processing unit 104, order information indicating foods and drinks ordered by the user to the second server 300. The memory 102 is achieved by a non-transitory storage device such as a flash memory. The communication unit 101 receives surrounding map information, which is map information regarding a surrounding area of a position of the information terminal 100 detected by the GPS sensor 107. The surrounding map information is displayed on the display 105.

The memory 102 stores, in advance, identification information for identifying the user.

The camera 103 is an imaging device achieved by a complementary metal-oxide-semiconductor (CMOS) sensor or the like. The camera 103 is used to capture an image of the user's face, for example, for face recognition.

The processing unit 104 is achieved by a processor such as a CPU. The processing unit 104 executes the OS of the information terminal 100, the matching app, a browser, and the like. The GPS sensor 107 detects the position of the information terminal 100 on the basis of a signal from a GPS satellite.

The display 105 is achieved by a liquid crystal display panel, an organic electroluminescent (EL) panel, or the like and displays various images. For example, the display 105 displays the menu information. The display 105 also displays the surrounding map information.

The operation unit 106 is achieved by an input device such as a touch panel. The operation unit 106 receives an operation performed by the user to select, among restaurants displayed in the surrounding map information, a restaurant that the user desires to visit. The operation unit 106 receives an instruction to select foods and drinks desired by the user in the menu information.

The configuration of the information terminal 100 has been described.

Next, the configuration of the first server 200 will be described. The first server 200 includes a communication unit 201, a processing unit 202, and a memory 203. The communication unit 201 is achieved by a communication circuit for connecting the first server 200 to the network NT. The communication unit 201 receives, from the information terminal 100, identification information for identifying the user of the information terminal 100 and a store ID indicating a second restaurant in a restaurant chain different from one to which a first restaurant belongs. The store ID is identification information regarding a store selected by the user who operates the information terminal 100. The communication unit 201 transmits individual menu information, which will be described later, generated by the processing unit 202 to the information terminal 100 owned by the user who has selected the second restaurant.

The processing unit 202 is achieved by a processor such as a CPU. The processing unit 202 processes personal information regarding the user stored in the memory 203.

The processing unit 202 provides the information terminal 100 with store information indicating one or more restaurants around the information terminal 100 owned by the user who has selected a second restaurant. The user of the information terminal 100 selects a second restaurant in the provided store information. The information terminal 100 transmits, to the first server 200, a store ID of the second restaurant selected by the user and the identification information regarding the user.

The processing unit 202 extracts, from the memory 203, taste information corresponding to the identification information regarding the user transmitted from the information terminal 100 and associated with the store ID. The processing unit 202 generates, on the basis of the extracted taste information and menu information regarding the second restaurant indicated by the store ID, individual menu information, which is meu information in which menu items are arranged in order according to the taste information. The individual menu information is displayed on the display 105 of the information terminal 100 owned by the user who has selected the second restaurant. The menu information regarding the second restaurant is standard menu information generated for a general customer in a restaurant chain to which the second restaurant belongs. In the standard menu information, menu items are arranged in certain order determined by the restaurant chain to which the second restaurant belongs. The menu items refer to foods and drinks served at the second restaurant.

If there are no order records, at the second restaurant, of the user who has selected the second restaurant, the processing unit 202 generates, on the basis of the taste information extracted from the memory 203 and the standard menu information, individual menu information in which the menu items included in the standard menu information are arranged in order according to the taste information. As a result, the user can efficiently select foods and drinks that suit his/her taste even when the user uses for a first time the restaurant chain to which the second restaurant belongs.

If there are order records, at the second restaurant, of the user who has selected the second restaurant, on the other hand, the processing unit 202 generates, on the basis of the order records at the second restaurant and the standard menu information regarding the second restaurant, individual menu information in which the menu items included in the standard menu information regarding the second restaurant are arranged in order according to the order records at the second restaurant. As a result, if the user has used the second restaurant before, the user can efficiently select foods and drinks that suit the user's taste using the individual menu information that reflects the order records at the second restaurant.

If the number of order records, at the second restaurant, of the user who has selected the second restaurant is smaller than a certain value, the processing unit 202 may generate, on the basis of the taste information corresponding to the identification information regarding the user and the standard menu information regarding the second restaurant, individual menu information in which the menu items included in the standard menu information regarding the second restaurant are arranged in the order according to the taste information.

In this case, if the number of order records, at the second restaurant, of the user who has selected the second restaurant is larger than or equal to the certain value, the processing unit 202 may generate, on the basis of the order records at the second restaurant and the standard menu information regarding the second restaurant, individual menu information in which the menu items included in the standard menu information regarding the second restaurant are arranged in order according to the order records at the second restaurant.

Furthermore, if a latest order record placed at the second restaurant by the user who has selected the second restaurant precedes a certain period, the processing unit 202 may generate, on the basis of the taste information corresponding to the identification information regarding the user and the standard menu information regarding the second restaurant, individual menu information in which the menu items included in the standard menu information regarding the second restaurant are arranged in the order according to the taste information.

The memory 203 is achieved by nonvolatile storage devices such as hard disk drives. The memory 203 stores personal information regarding one or more users. The personal information includes taste information regarding the users. The taste information indicates the users' taste. The taste information includes order records of the users for foods and drinks. In the present embodiment, order records are managed in an order record database D2 illustrated in FIG. 12 generated for each of the users and stored in the memory 203.

Activity record information indicates activity records of the users. Personal information is stored in the storage devices while being split and encrypted. The personal information stored in the memory 203 may include biological information, purchase record information, and the activity record information as well as the taste information. The biological information is information relating to each user's body, such as heart rate. The purchase record information indicates each user's records of purchasing products (articles) or services. The activity record information is, for example, time series data in which positional information regarding each user and time information are associated with each other.

Next, the configuration of each of the second servers 300 will be described. There are one or more second servers 300 for each restaurant chain. Each of the second servers 300 includes a communication unit 301, a processing unit 302, and a memory 303. The communication unit 301 is achieved by a communication circuit for connecting the second server 300 to the network NT. The communication unit 301 transmits standard menu information to the first server 200 in response to a request from the information terminal 100. The processing unit 302 is achieved by a processor such as a CPU. The processing unit 302 processes standard menu information stored in the memory 303. The memory 303 is achieved by a nonvolatile storage device such as a hard disk drive. The memory 303 stores the standard menu information.

Ordering for Foods and Drinks Based on Individual Menu Information

Figure 3:
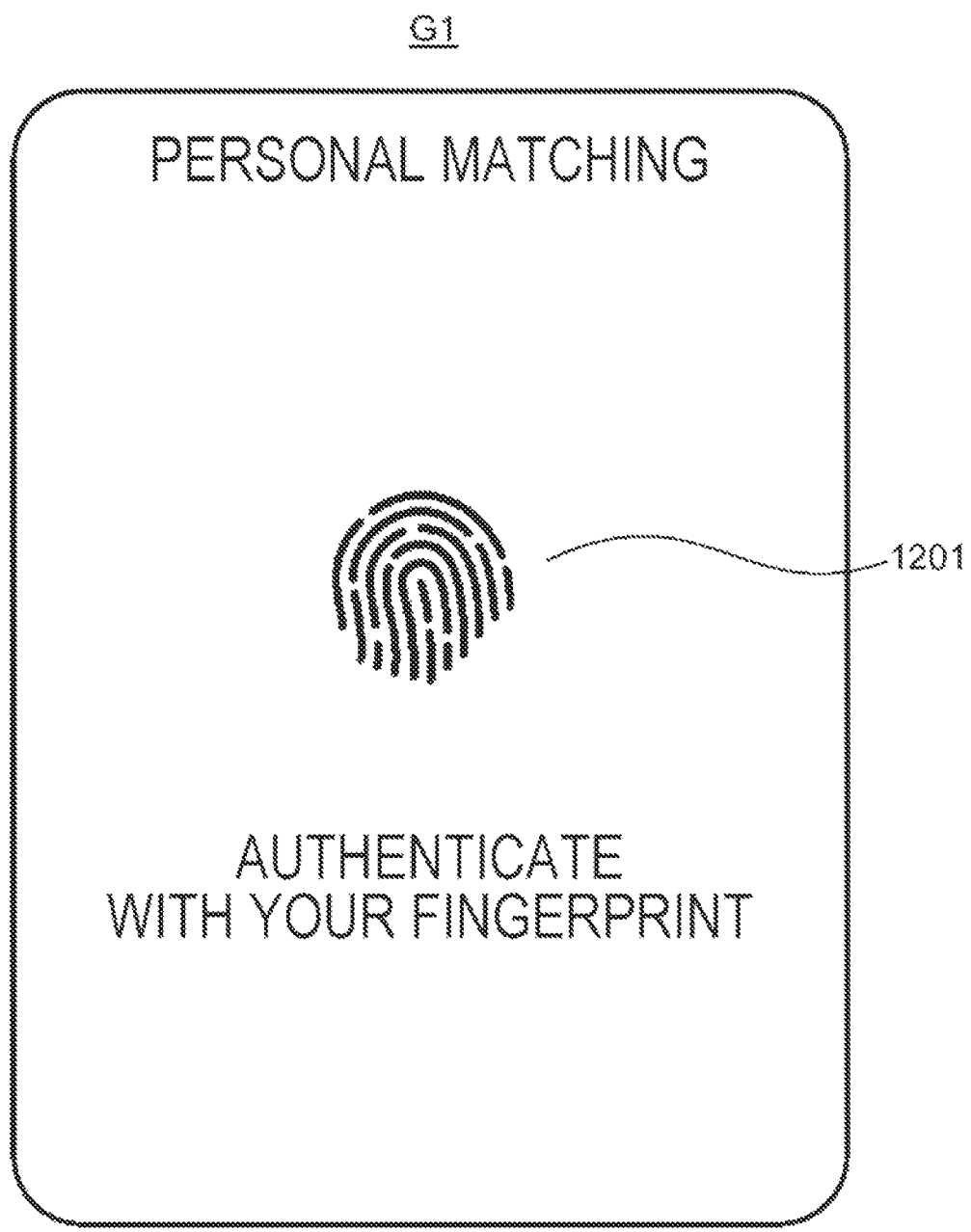
FIG. 3 is a diagram illustrating an example of an authentication screen displayed on an information terminal immediately after a user who is to order foods and drinks activates a matching app.

Ordering for foods and drinks based on individual menu information starts when the matching app is activated. FIG. 3 is a diagram illustrating an example of an authentication screen G1 displayed on the information terminal 100 immediately after the user who is to order foods and drinks activates the matching app. The authentication screen G1 is a screen on which the user is authenticated through fingerprint recognition. A fingerprint image 1201 schematically indicating a fingerprint is displayed at the center of the authentication screen G1, and a message, "Authenticate with your fingerprint", is displayed under the fingerprint image 1201. The authentication screen G1 thus prompts the user to perform fingerprint recognition. "Personal matching" is displayed at a top of the authentication screen G1. The user can thus understand that the authentication screen G1 is a screen of the matching app. This holds true for FIGS. 4 and 5, which will be referred to later.

Figure 4:
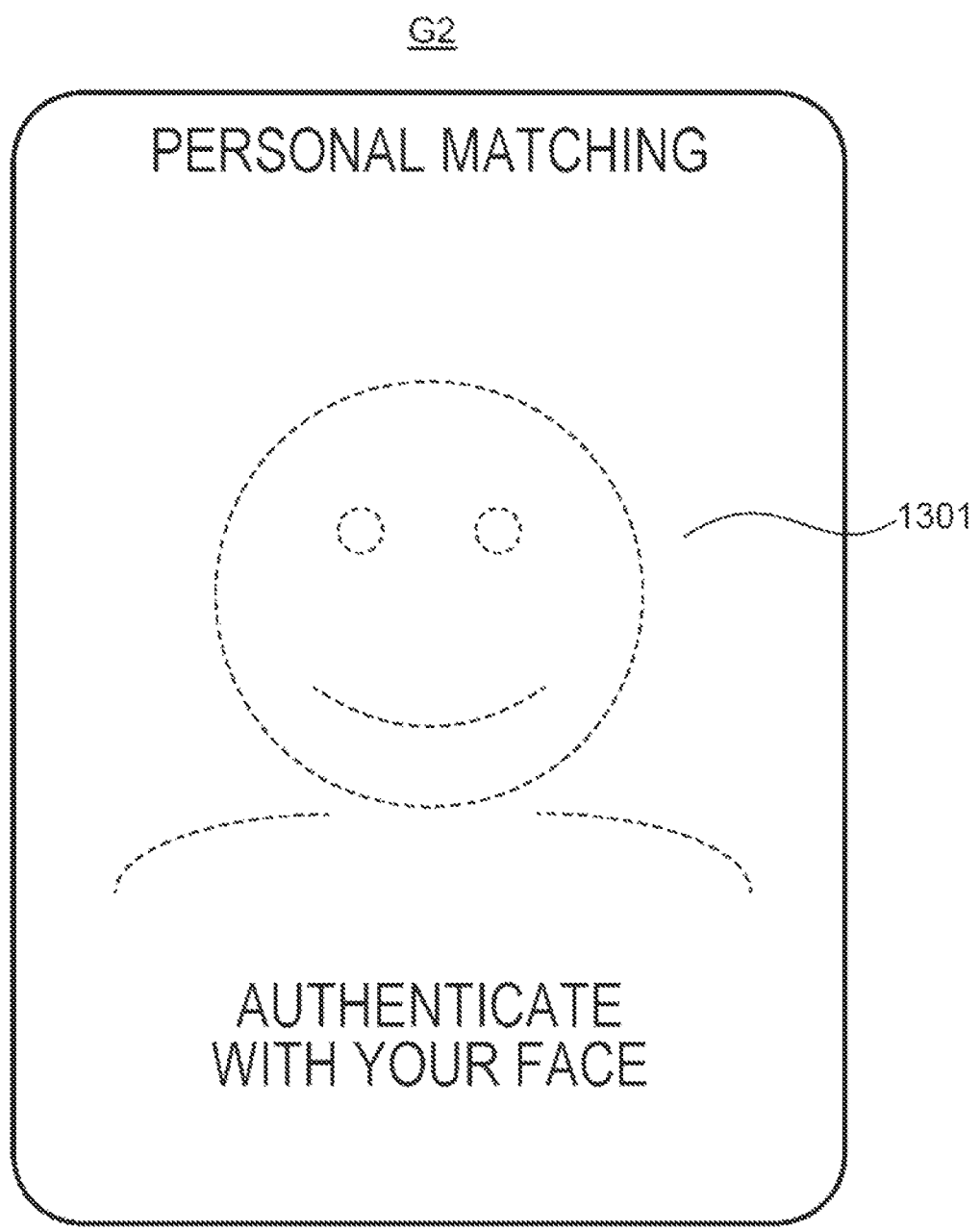
FIG. 4 is a diagram illustrating an authentication screen in another example.

FIG. 4 is a diagram illustrating an authentication screen G2 in another example. The authentication screen G2 is an example of a screen for authenticating the user through face recognition. Broken lines 1301 schematically indicating a contour of a face are displayed at the center of the authentication screen G2 so that the information terminal 100 can capture an image of the user's face from the front in an appropriate size. The user adjusts a direction and a position of the information terminal 100 such that the user's face from the front fits into the broken lines 1301.

If there is a method for authenticating the user by which necessary authentication accuracy can be achieved with a smaller burden on the user than the above methods for authenticating the user, the method may be employed, instead. As a method for authenticating the user, two-step authentication, which is generally said to have high security strength, may be employed, or a method in which a user ID and a password are input may be employed, instead.

Figure 5:
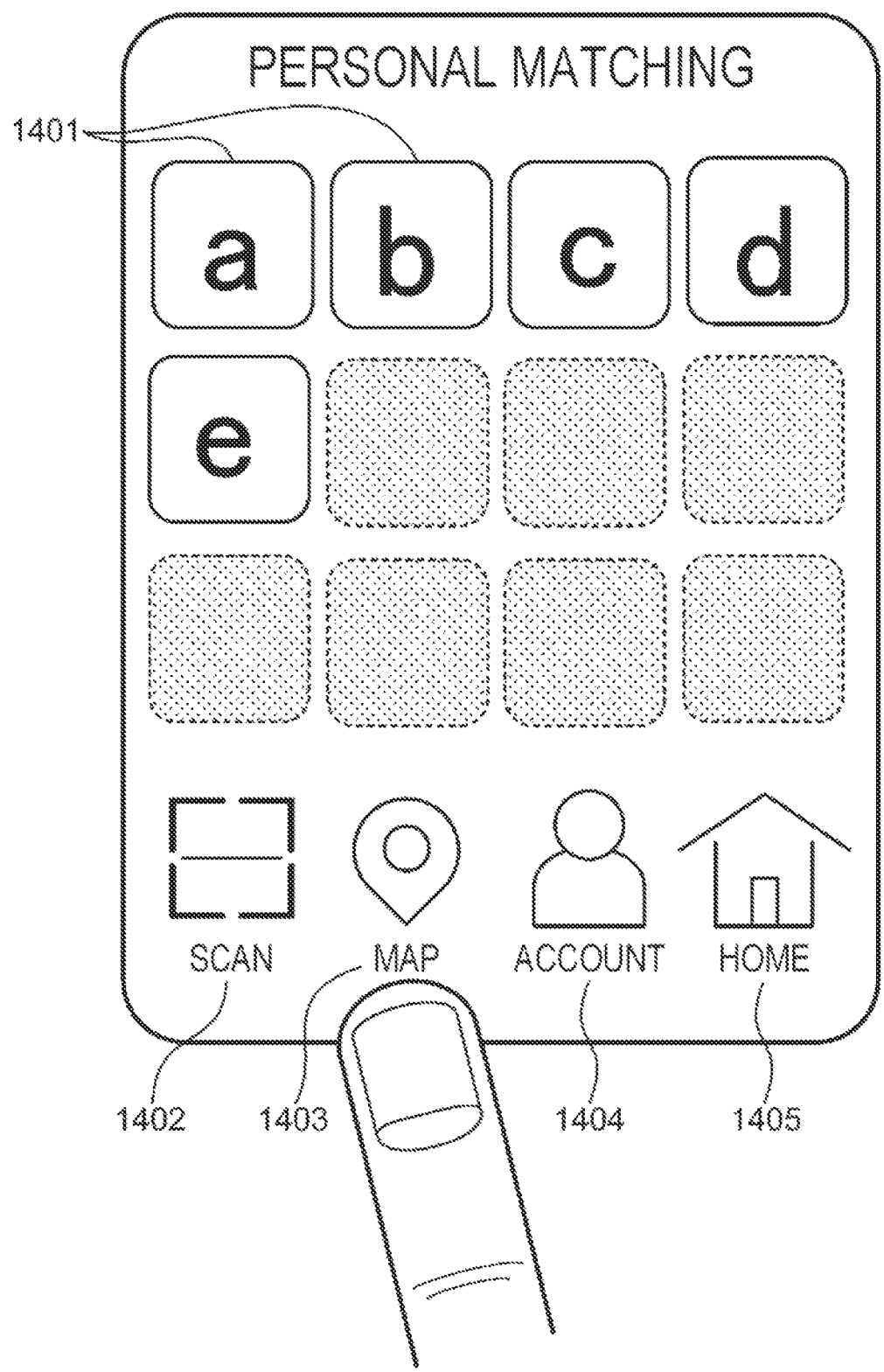
FIG. 5 is a diagram illustrating an example of a home screen displayed immediately after the user is authenticated for the matching app.

FIG. 5 is a diagram illustrating an example of a home screen G3 displayed immediately after the user is authenticated for the matching app. An app name "personal matching" is displayed at a top of the home screen G3, and tile objects 1401 are arranged in a middle in a matrix. The tile objects 1401 are associated with association functions or other applications incorporated into the matching app. The other applications are, for example, applications activated in the matching app. In this example, five tile objects 1401 indicated by a, b, c, d, and e are displayed. These tile objects 1401 are associated with dedicated functions (e.g., applications of certain restaurants available in the matching app) for matching with products or services of various business operators in association with the matching app. The user can thus use the five association functions indicated by a, b, c, d, and e. Grayed-out tile objects 1401 are vacant tile objects for which no association function has been installed. A scan button 1402, a map button 1403, an account button 1404, and a home button 1405 are displayed at a bottom of the home screen G3 from the left. These four buttons are fixed buttons provided for all users. The scan button 1402 is used to read a quick response (QR) code (registered trademark), a near-field communication (NFC) tag, a radio-frequency identification (RFID) tag, or the like associated with a service provided by a business operator such as a restaurant. The map button 1403 is used to display a map screen including store information regarding stores that are located around the current position of the information terminal 100 and that have registered with the matching app and/or information regarding products or services provided at the stores. The account button 1404 is used to register and edit account information regarding the user. The registration and editing of the account information include, for example, settings for personal authentication and settings for the association functions with the first server 200. The home button 1405 is used to return to the home screen G3.

As described above, the tile objects 1401 indicating the dedicated functions for associating with services provided by other business operators through the matching app are arranged in the middle of the home screen G3. The user can display, remove, or move these tile objects 1401 as desired. The user, therefore, can obtain, among products and/or services provided by a large number of business operators (e.g., appliance stores, digital versatile disc (DVD) and Blu-ray disc (registered trademark) rental stores, bookstores, coffee shops, taxis, etc.), products and/or services suitable for the user on the basis of personal information using a matching app.

Figure 6:
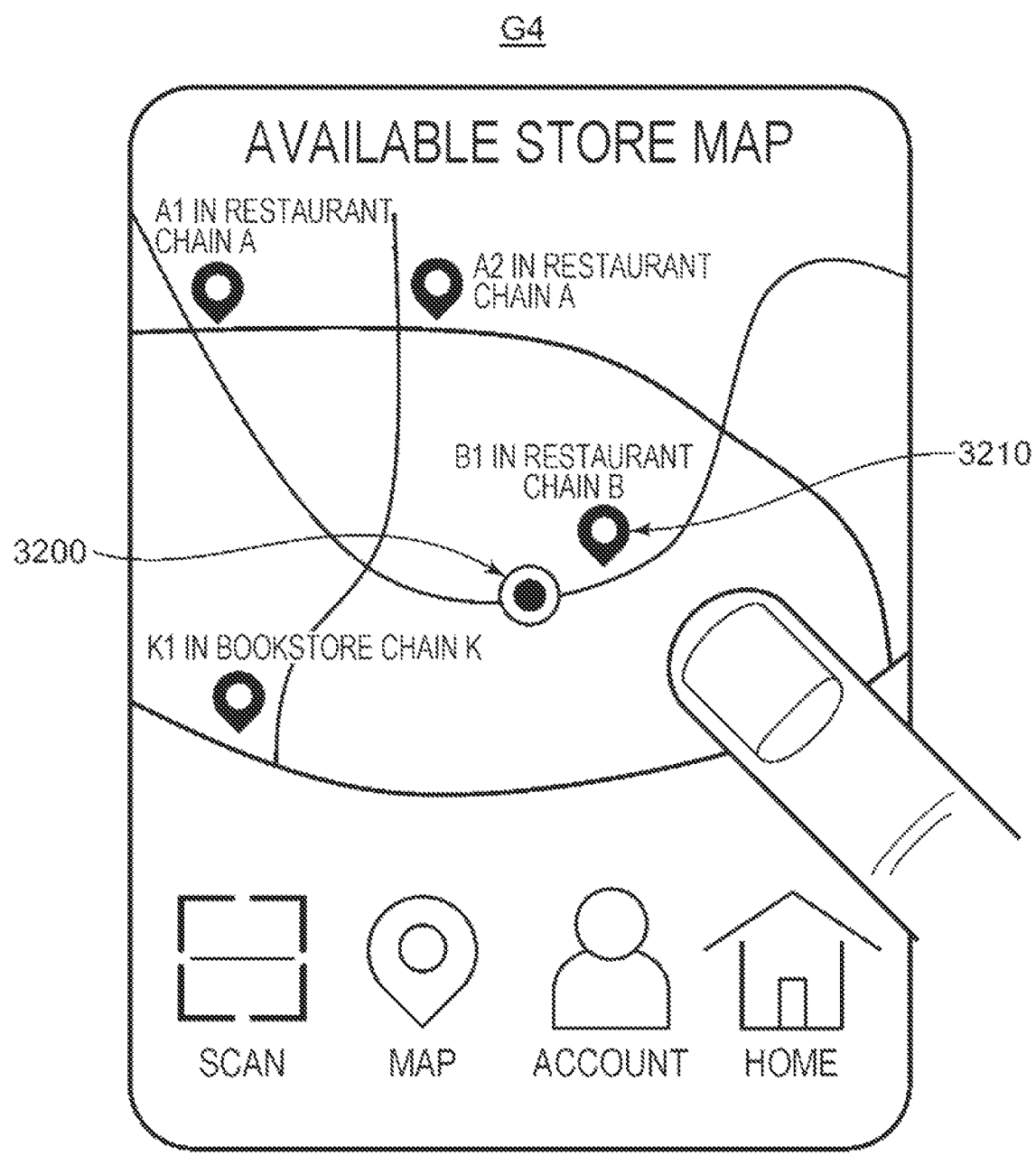
FIG. 6 is a diagram illustrating an example of a map screen displayed on the information terminal.

FIG. 6 is a diagram illustrating an example of a map screen G4 displayed on the information terminal 100. The map screen G4 is displayed when the user selects the map button 1403 in the home screen G3. The map screen G4 includes a map of an area including the current position of the information terminal 100. Store information in the area available in the matching app is also displayed in the map screen G4. Here, an icon 3200 indicating a current position of the user, stores A1 and A2 in restaurant chain A, store K1 in bookstore chain K, and store B1 in restaurant chain B are displayed.

The user selects a store to visit on the map screen G4. In this example, the user selects store B1, which is indicated by an icon 3210, in restaurant chain B closest to the current position thereof. The user touches the icon 3210, for example, to select store B1 in restaurant chain B. The user touches the icon 3210, and the matching app obtains connection information regarding store B1 in restaurant chain B indicated by the icon 3210 and a store ID of store B1. The matching app also obtains the identification information (user ID) regarding the user from the memory 102. As described later with reference to FIG. 18, the user ID is stored in a "user_account.xml" file under an "account" directory of the information terminal 100. The connection information is, for example, address information (e.g., a URL) for communicating with the second server 300 for restaurant chain B.

The matching app obtains individual menu information for the user on the basis of the obtained store ID and user ID in cooperation with the first server 200 and the second server 300 for restaurant chain B.

More specifically, the matching app transmits, to the first server 200, a request to obtain an individual menu including the store ID and the user ID. Upon receiving the request, the first server 200 transmits, to the second server 300 for restaurant chain B on the basis of the store ID, a request to obtain standard menu information regarding a standard menu that can be provided by store B1. Upon receiving the request, the second server 300 transmits the standard menu information regarding restaurant chain B to the first server 200. The standard menu information is stored in a "ResB.html" file and a "ResB.css" file of the second server 300, which will be described later with reference to FIG. 18.

Upon receiving the standard menu information regarding restaurant chain B, the first server 200 obtains, from the memory 203, order records of the user at restaurant chain B in order to optimize the obtained standard menu information for the user corresponding to the user ID. It is assumed here that the memory 203 does not store order records of the user at restaurant chain B.

In this case, for example, the first server 200 obtains, from the memory 203, order records of the user at another restaurant chain. The first server 200 then changes order of display of foods and drinks in the standard menu of restaurant chain B such that foods and drinks ordered more by the user in the order records at the other restaurant are displayed earlier. It is assumed, for example, that the user has frequently ordered "caffe mocha" at another restaurant. In this case, the first server 200 displays "caffe mocha" earlier in the individual menu information regarding restaurant chain B so that the user can easily order "caffe mocha". Furthermore, in this case, the first server 200 may change a mode in which "caffe mocha" is displayed from a default mode so that the user can easily find "caffe mocha" on the basis of the size and/or color of letters "caffe mocha".

The first server 200 transmits the individual menu information regarding restaurant chain B generated in the above manner to the information terminal 100.

Figure 7:
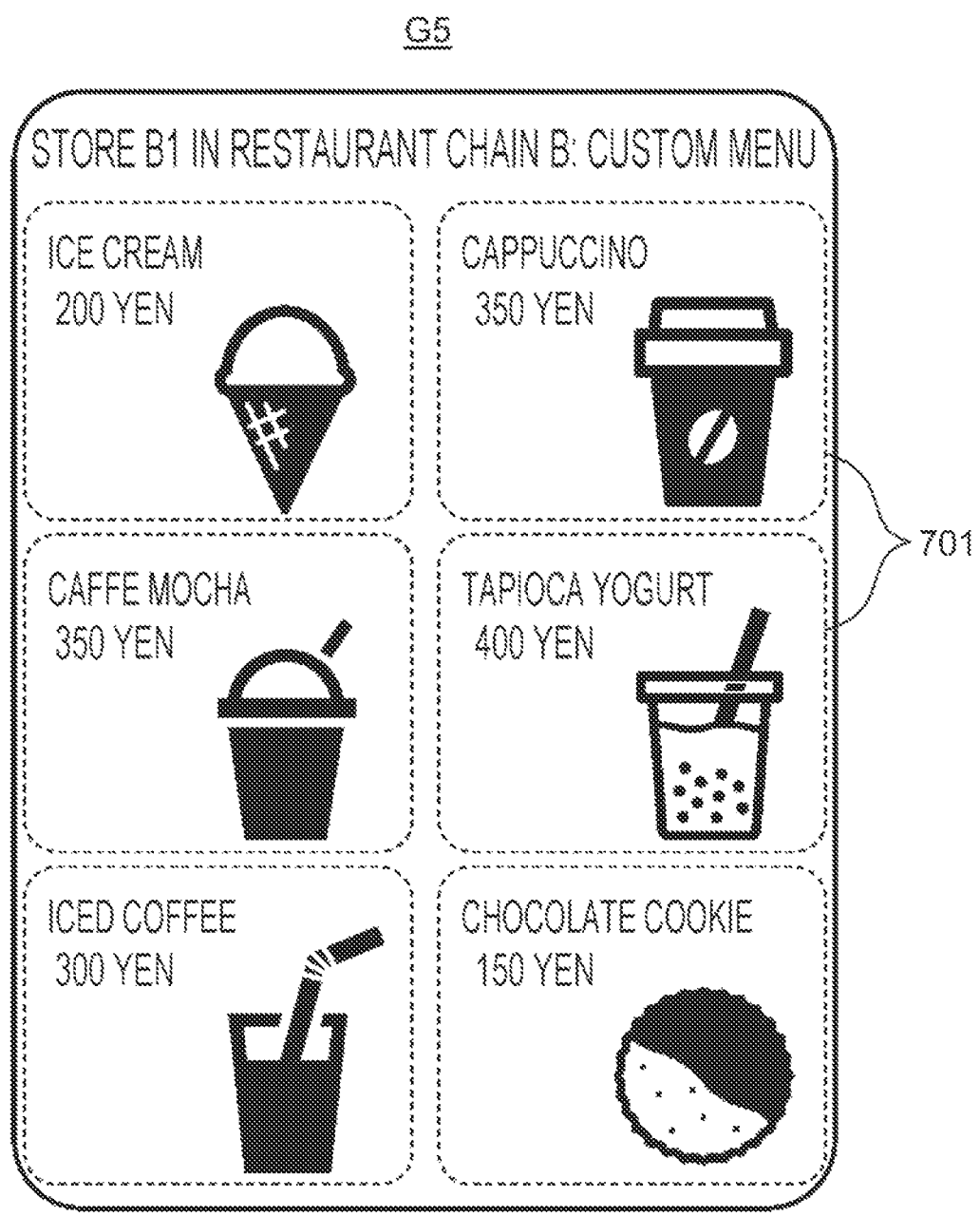
FIG. 7 is a diagram illustrating an individual menu screen, which is an example of a display screen for individual menu information displayed on the information terminal.

FIG. 7 is a diagram illustrating an individual menu screen G5, which is an example of a display screen for individual menu information displayed on the information terminal 100. The individual menu screen G5 is an individual menu screen for restaurant chain B selected by the user on the map screen G4. "Restaurant chain B store B1 custom menu" is displayed at a top of the individual menu screen G5. This means that a menu in the individual menu screen G5 is a menu personalized in consideration of the standard menu information regarding restaurant chain B to which store B1 selected by the user belongs and the order records of the user stored in the memory 203.

In this example, the memory 203 does not store order records of the user at restaurant chain B but stores order records of the user at another restaurant chain. The order records of the user at the other restaurant chain indicate that the user has ordered ice cream, cappuccino, caffe mocha, tapioca yogurt, iced coffee, and a chocolate cookie more in this order. In the individual menu screen G5, therefore, tile objects 701 indicating the foods and the drinks are arranged in this order.

Since foods and drinks that suit the user's taste are displayed at such positions that the user can easily order the foods and the drinks, the user can efficiently select foods and drinks that suit his/her taste. In the example illustrated in FIG. 7, priority of display of the tile objects 701 is the highest at an upper-left position and the lowest at a lower-right position. This, however, is just an example, and priority of display may be the highest at an upper-right position and the lowest at a lower-left position, instead.

Although the tile objects 701 are displayed in a matrix of three rows and two columns in the example illustrated in FIG. 7, this is just an example. The tile objects 701 may be displayed in a matrix of three rows and one column or four rows and two columns, instead. Furthermore, in the example illustrated in FIG. 7, tile objects 701 indicating foods and drinks that are not displayed in an initial screen can be displayed through scrolling. The initial screen refers to a screen displayed first when the individual menu screen G5 is displayed.

Alternatively, design of the individual menu screen G5 with which the user can easily order foods and drinks may be as follows. For example, tile objects 701 indicating foods and drinks ordered most may be displayed in the initial screen of the individual menu screen G5, for example, and, in the initial screen, tile objects 701 indicating foods and drinks ordered most may be arranged at the center. After the tile objects 701 are arranged in such a manner, tile objects 701 indicating foods and drinks ordered most may be displayed larger, in a different color, with a different thickness of boundary lines, and/or with item names, prices, and/or item images decorated.

Figure 8:
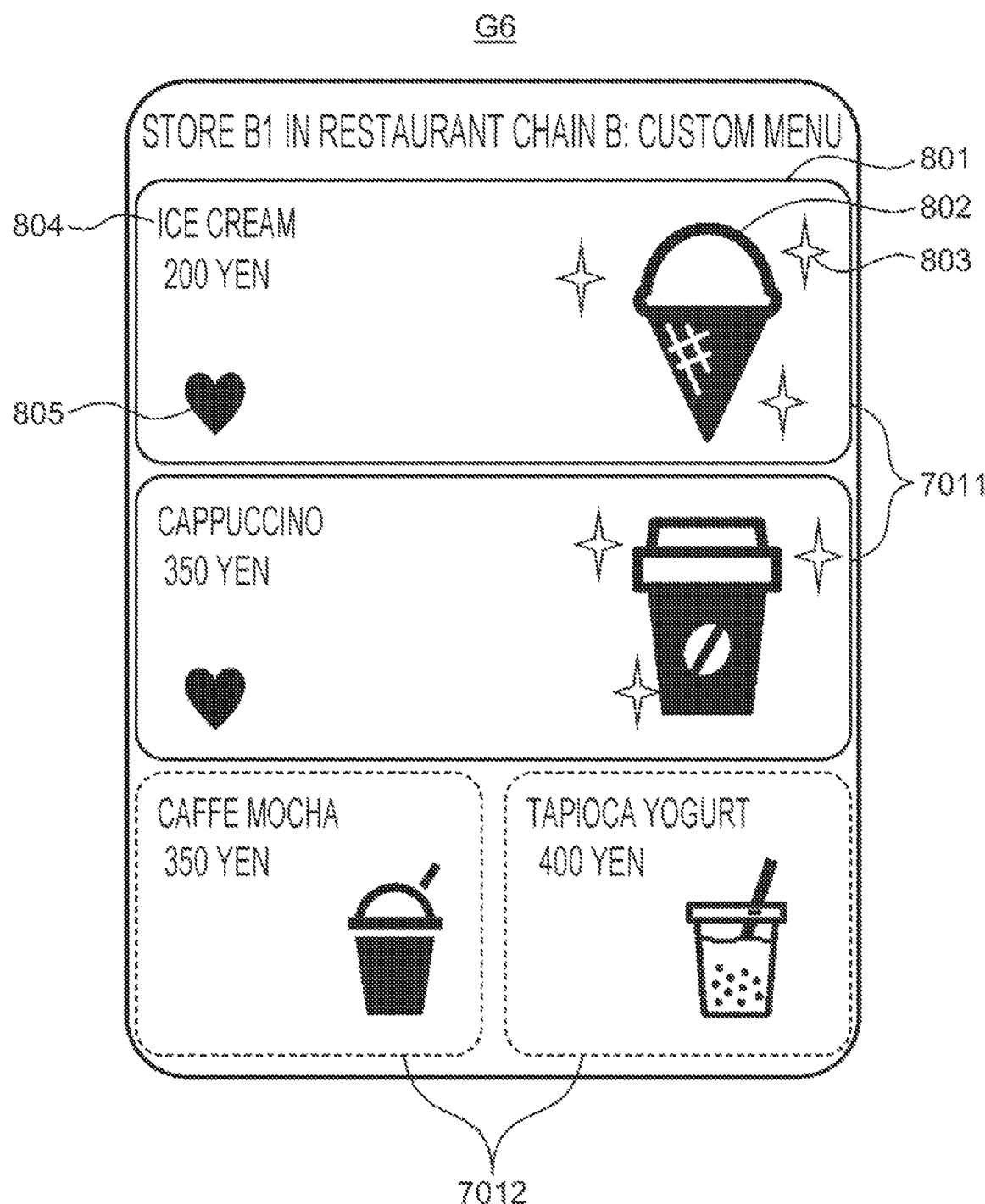
FIG. 8 is a diagram illustrating an individual menu screen, which is another example of the display screen for individual menu information displayed on the information terminal.

FIG. 8 is a diagram illustrating an individual menu screen G6, which is another example of the display screen for individual menu information displayed on the information terminal 100. In the individual menu screen G6, tile objects 7011 indicating a certain number of (here, top two) foods and drinks (here, ice cream and cappuccino) ordered most are arranged above tile objects 7012 indicating other foods and drinks (here, caffe mocha and tapioca yogurt). The tile objects 7012 indicating caffe mocha and tapioca yogurt are arranged in a third row of the individual menu screen G6.

The tile objects 7011 are also displayed larger than the tile objects 7012. Furthermore, frames 801 of the tile objects 7011 are thicker than ones of the tile objects 7012 and decorated. The frames 801 may be decorated, for example, a mode in which the frames 801 are displayed in a prominent color such as gold or red. Furthermore, images 802 in the tile objects 7011 indicating foods and drinks are larger than ones in the tile objects 7012. Furthermore, in the tile objects 7011, marks 803 (here, star marks) for highlighting the images 802 indicating foods and drinks are displayed. Furthermore, in the tile objects 7011, character strings 804 indicating names of foods and drinks are displayed larger than in the tile objects 7012. The character strings 804 may be highlighted by giving shadows, instead. Furthermore, in the tile objects 7011, marks 805 (here, heart marks) indicating favorites are displayed.

In FIG. 8, a reason why the tile object 7011 indicating ice cream is arranged above the tile object 7011 indicating cappuccino is that the user has ordered ice cream more than cappuccino. In FIG. 8, tile objects 7012 indicating foods and drinks that are not displayed in an initial screen may be displayed through scrolling. In this case, the user may vertically scroll the individual menu screen G6 to move all tile objects vertically. Alternatively, the user may horizontally scroll a field where the tile objects 7012 are displayed to move only the tile objects 7012 with the tile objects 7011 fixed.

Figure 9:
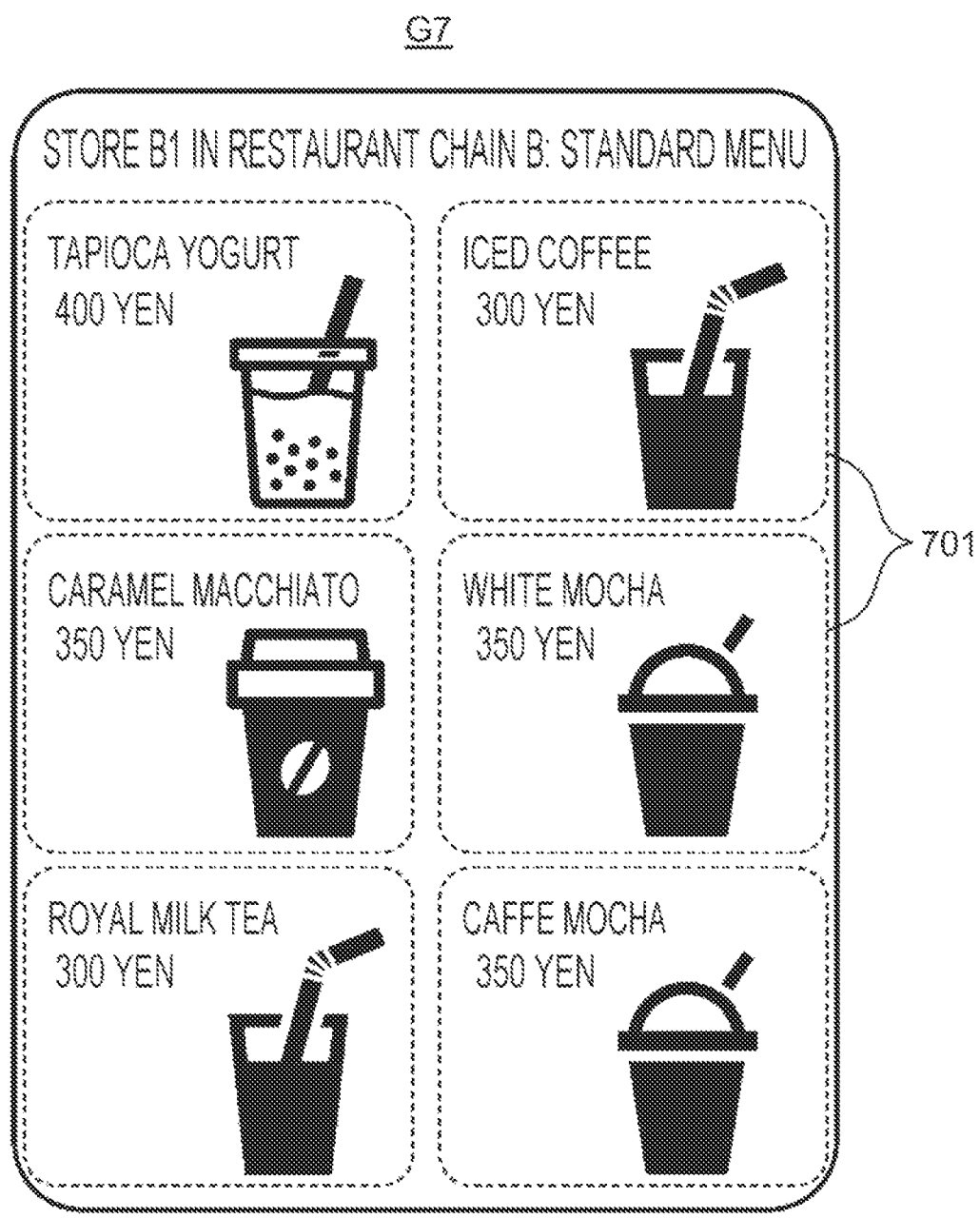
FIG. 9 is a diagram illustrating a standard menu screen, which is an example of a display screen for standard menu information displayed on the information terminal.

FIG. 9 is a diagram illustrating a standard menu screen G7, which is an example of a display screen for standard menu information displayed on the information terminal 100. In the standard menu screen G7, standard menu information regarding store B1 in restaurant chain B, which is not optimized for each user, is displayed.

"Restaurant chain B store B1 standard menu" is displayed at a top of the standard menu screen G7. This means that a menu displayed in the standard menu screen G7 is a standard menu of restaurant chain B. Tile objects 701 are arranged in the standard menu screen G7, for example, in a matrix of three rows and two columns. Here, tile objects 701 indicating popular foods and drinks of restaurant chain B are arranged at such positions that the user can easily order the foods and the drinks. More specifically, tile objects 701 indicating most popular foods and drinks are arranged at upper-left positions, and tile objects 701 indicating least popular foods are arranged at lower-right positions. The standard menu screen G7 is configured to display, through scrolling, tile objects 701 that are not displayed in an initial screen.

The tile objects 701 are arranged in the standard menu screen G7 without taking into consideration taste information regarding each of the users, and it is troublesome for the user to find tile objects 701 indicating desired foods and drinks.

In the individual menu screens G5 and G6, on the other hand, foods and drinks that suit the user's taste are arranged at such positions that the user can easily order the foods and the drinks, and it is more likely for the user to be able to easily find tile objects 701 indicating foods or drinks that the user desires. Furthermore, in the individual menu screens G5 and G6, tile objects 701 indicating foods and drinks most ordered by the user are displayed at positions of highest priority on the basis of the order records of the user stored in the first server 200. Even if the user has not used not only store B1 selected by the user but also any of stores in restaurant chain B, to which store B1 belongs, therefore, the tile objects 701 are arranged in the individual menu screens G5 and G6 in order that takes into consideration the user's taste.

It is assumed, for example, that the user frequently visits store A1 in restaurant chain A and the user has ordered foods and drinks at store A1 while displaying an individual menu screen that takes into consideration order records thereof on the information terminal 100. In this case, even if the user visits store B1 in restaurant chain B for a first time, the user can display, on the information terminal 100, the individual menu screen G5 or G6, in which foods and drinks are arranged in order similar to that in the individual menu screen for familiar restaurant chain A. As a result, the user can promptly find desired foods and drinks and feel comfortable. Furthermore, since an individual menu screen in which foods and drinks are arranged in familiar order is displayed even at a store in a chain that the user visits for a first time, the user will be surprised and get more interested in ordering.

Figure 10:
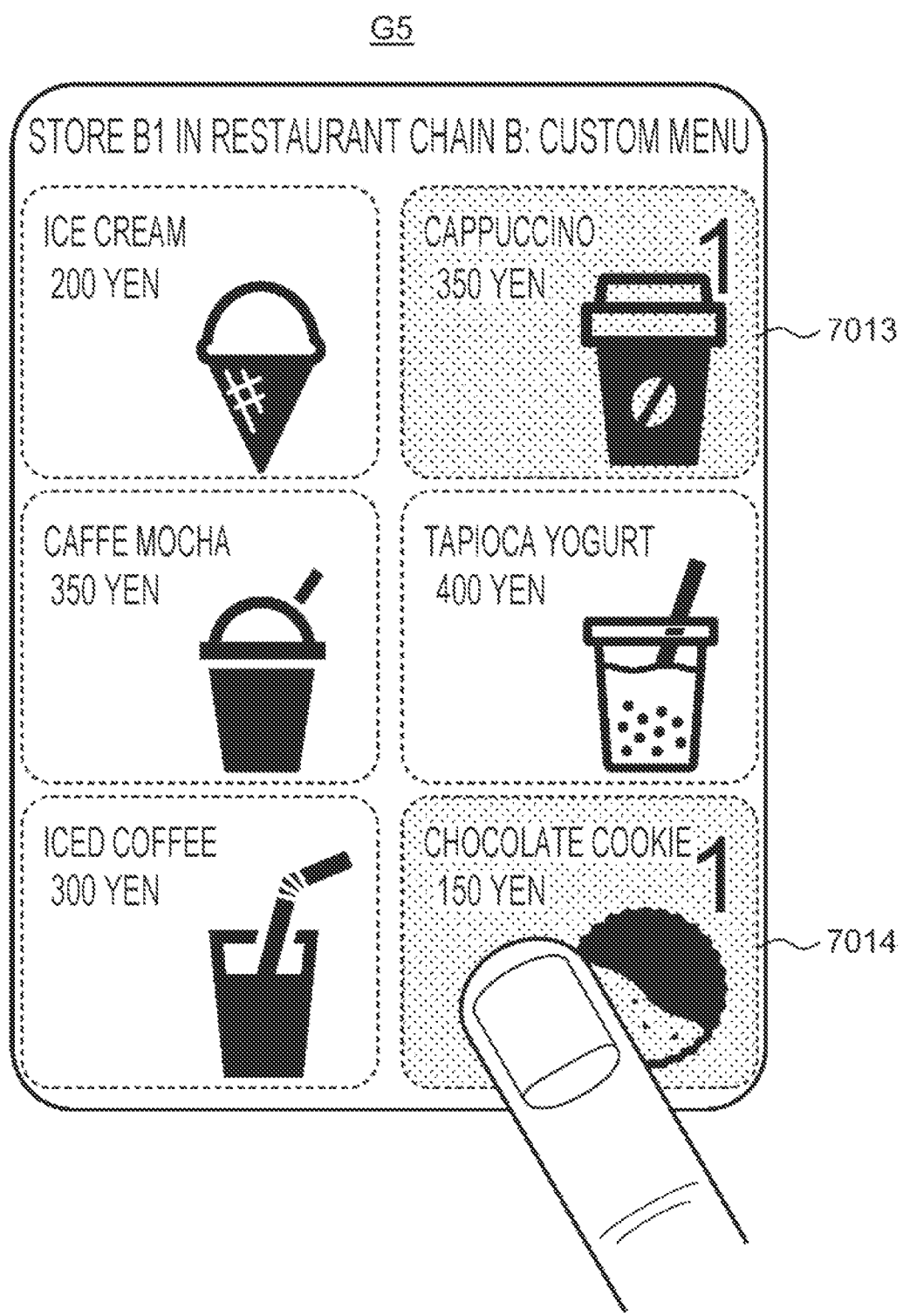
FIG. 10 is a diagram illustrating how the user orders a food and a drink on the individual menu screen illustrated in FIG. 7.

FIG. 10 is a diagram illustrating how the user orders a food and a drink on the individual menu screen G5 illustrated in FIG. 7. Here, the user selects a tile object 7013 indicating cappuccino and a tile object 7014 indicating a chocolate cookie. A color of the tile objects 7013 and 7014, therefore, is changed from a first color to a second color, which indicates that a corresponding item has been selected. Furthermore, since the tile objects 7013 and 7014 have been selected once each, numbers "1", which indicate the number of items ordered using the tile objects 7013 and 7014, are displayed.

Figure 11:
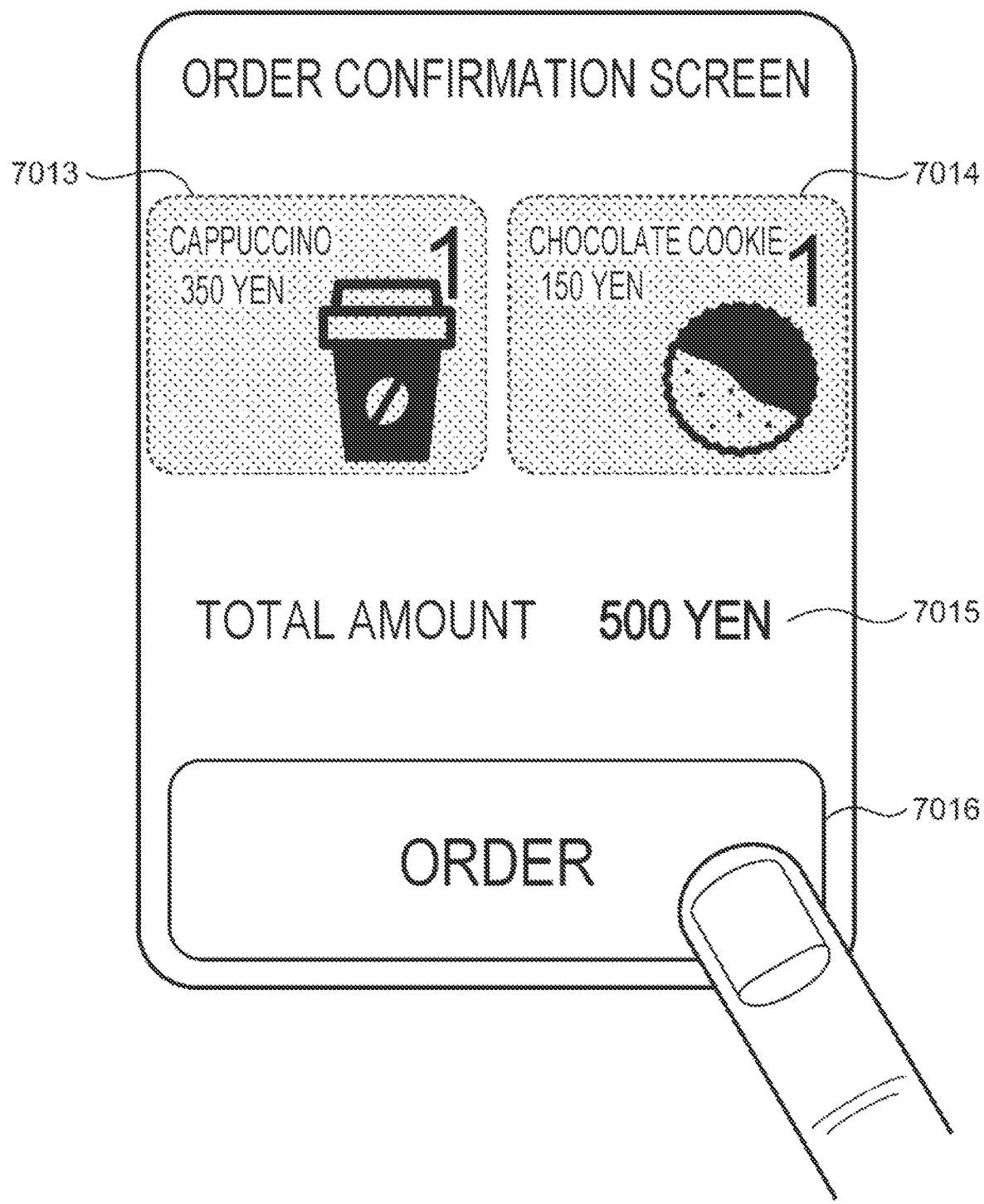
FIG. 11 is a diagram illustrating an example of an order confirmation screen displayed when the user confirms the order of the food and the drink selected in FIG. 10.

FIG. 11 is a diagram illustrating an example of an order confirmation screen G8 displayed when the user confirms the order for the food and the drink selected in FIG. 10. The order confirmation screen G8 is displayed when the user presses a "proceed to order" button, which is not illustrated, in the individual menu screen G5 illustrated in FIG. 10. In the order confirmation screen G8, the tile object 7013 indicating cappuccino and the tile object 7014 indicating a chocolate cookie selected in the individual menu screen G5 are displayed. A total amount field 7015 indicating the total amount of money to be paid for the food and the drink is displayed under the tile objects 7013 and 7014. Since the user has selected one cappuccino and one chocolate cookie and the total amount is 500 yen, "500 yen" is displayed in the total amount field 7015. An order button 7016 for confirming the order is displayed under the total amount field 7015. The user who is satisfied with details of the order displayed in the order confirmation screen G8 touches the order button 7016 to complete the order.

Ordering

Figure 15:
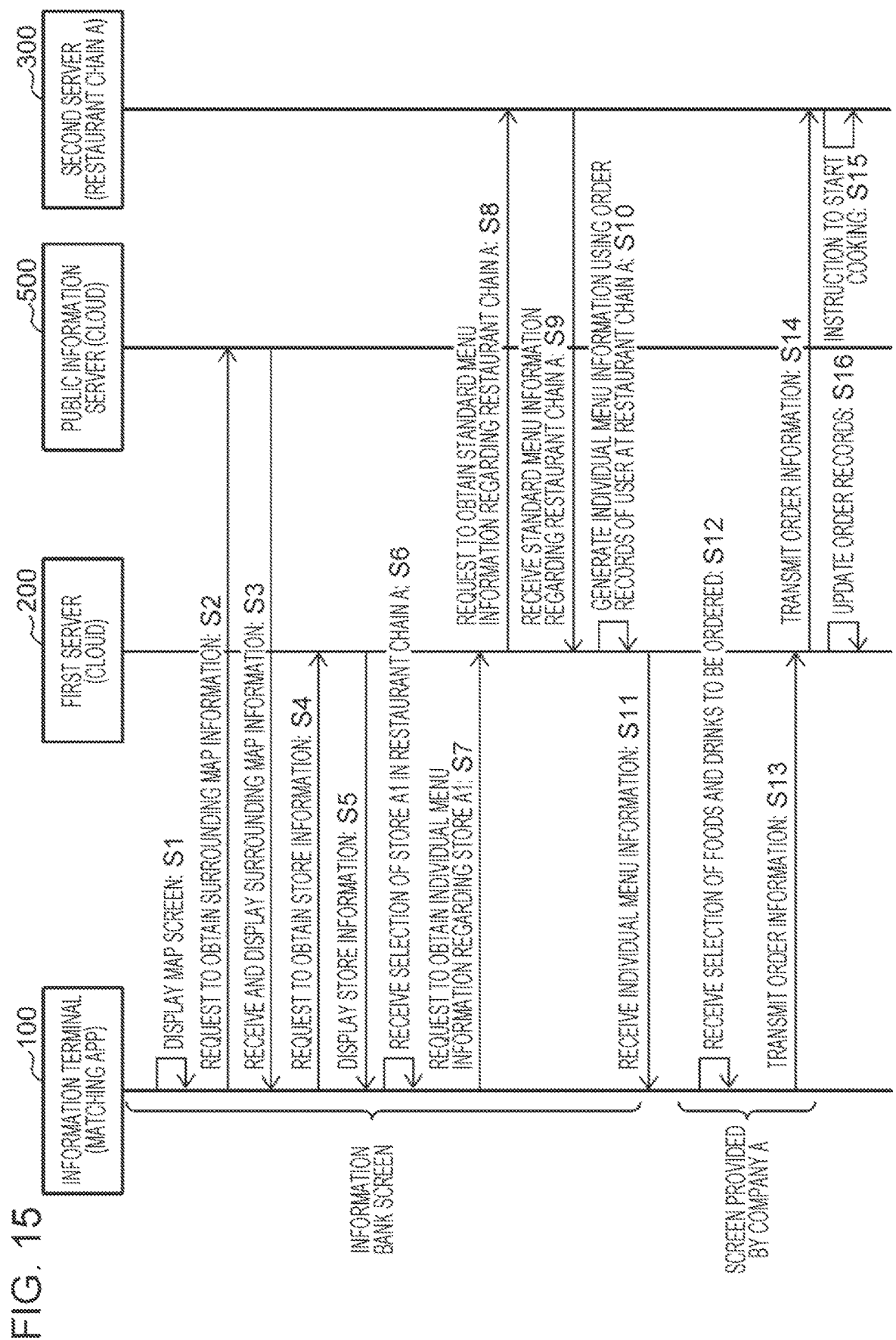
FIG. 15 is a sequence diagram illustrating an example of a process performed by the information provision system when the user who is visiting a store in a familiar chain orders foods and drinks.

FIG. 15 is a sequence diagram illustrating an example of a process performed by the information provision system when the user who is visiting a store in a familiar chain orders foods and drinks.

In step S1, the information terminal 100 receives an instruction to activate the matching app from the user, activates the matching app, and displays the map screen G4 on the display 105. More specifically, when activated, the matching app displays the authentication screen G1 or G2 and authenticates the user. If the user is successfully authenticated, the matching app displays the home screen G3. If the user touches the map button 1403 in the home screen G3, the matching app displays the map screen G4.

In step S2, the matching app obtains positional information indicating the current position of the information terminal 100 detected by the GPS sensor 107 and transmits, to the public information server 500, a request to obtain surrounding map information, which is map information regarding a surrounding area including the position.

Upon receiving the request, the public information server 500 obtains the current position of the information terminal 100 from the positional information included in the request, extracts, from a map database, map information regarding an area within a certain range from the position as surrounding map information, and transmits the map information to the matching app. Upon receiving the surrounding map information, the matching app displays the map screen G4 including a map indicated by the surrounding map information (step S3). The certain range indicating the area is a range within which the user who is going to eat out can visit a store on foot or by car from the current position, such as a radius of 1 km or 2 km.

After displaying the map screen G4, the matching app transmits, to the first server 200, a request to obtain store information regarding stores that are included in the map indicated by the received surrounding map information and that are registered in the first server 200 (step S4).

Upon receiving the request, the first server 200 extracts store information regarding stores included in the map from the memory 203 and transmits the store information to the matching app. The memory 203 stores a store database including store information regarding stores. The store information includes a store ID and a name of each of the stores, a chain to which the store belongs, and positional information and connection information regarding the store. The first server 200, therefore, may identify stores included in the area of the map indicated by the request to obtain store information from the positional information regarding stores stored in the store database.

Upon receiving the extracted store information, the matching app displays the store information on the map in the map screen G4 (step S5). As a result, as indicated by the map screen G4 illustrated in FIG. 6, stores included in a surrounding area of the current position of the user are displayed on the map indicating the surrounding area.

In step S6, the matching app receives an instruction given by the user to select store A1 in restaurant chain A among the stores displayed in the map screen G4. It is assumed here that the user frequently visits store A1.

In step S7, the matching app transmits a request to obtain individual menu information regarding store A1 to the first server 200. The request includes a store ID of store A1, connection information regarding store A1, a user ID of the information terminal 100, and the like.

Upon receiving the request, the first server 200 transmits, to a second server 300 for restaurant chain A or store A1, a request to obtain standard menu information regarding restaurant chain A to which store A1 belongs (step S8).

Upon receiving the request, the second server 300 of restaurant chain A or store A1 transmits standard menu information regarding store A1 to the first server 200. The first server 200 receives the standard menu information regarding store A1 (step S9). The standard menu information regarding store A1 transmitted here may be menu information common to stores in restaurant chain A or menu information partly different between the stores in restaurant chain A.

Upon receiving the standard menu information regarding store A1, the first server 200 collects order records, at the stores in restaurant chain A, of the user stored in the memory 203 and generates individual menu information regarding store A1 (step S10). The first server 200 transmits the generated individual menu information regarding store A1 to the information terminal 100 (matching app), and the matching app receives the individual menu information (step S11).

In the steps up to step S11, various screens displayed on the information terminal 100 are designed in a style defined by a manager (information bank) of the first server 200. In step S12 and later steps, however, various screens displayed on the information terminal 100 are designed in a style defined by restaurant chain A.

In step S12, the matching app displays an individual menu screen indicating the received individual menu information regarding store A1 and receives, from the user, an instruction to select foods and drinks to be ordered.

In step S13, the matching app transmits order information indicating ordered foods and drinks to the first server 200. Upon receiving the order information, the first server 200 transmits the order information to the second server 300 for restaurant chain A (step S14). Upon receiving the order information, the second server 300 instructs, by displaying the order information on a display of a store terminal of store A1, for example, a staff member at store A1 to start cooking (step S15).

In step S16, the first server 200 stores the order information in the memory 203 to update the order records of the user (step S16).

Although a server with which the matching app communicates in the steps other than the obtaining of surrounding map information is the first server 200 in the sequence diagram of FIG. 15, the present disclosure is not limited to this. For example, the matching app may access a third server other than the first server 200 in order to obtain store information, instead.

Figure 16:
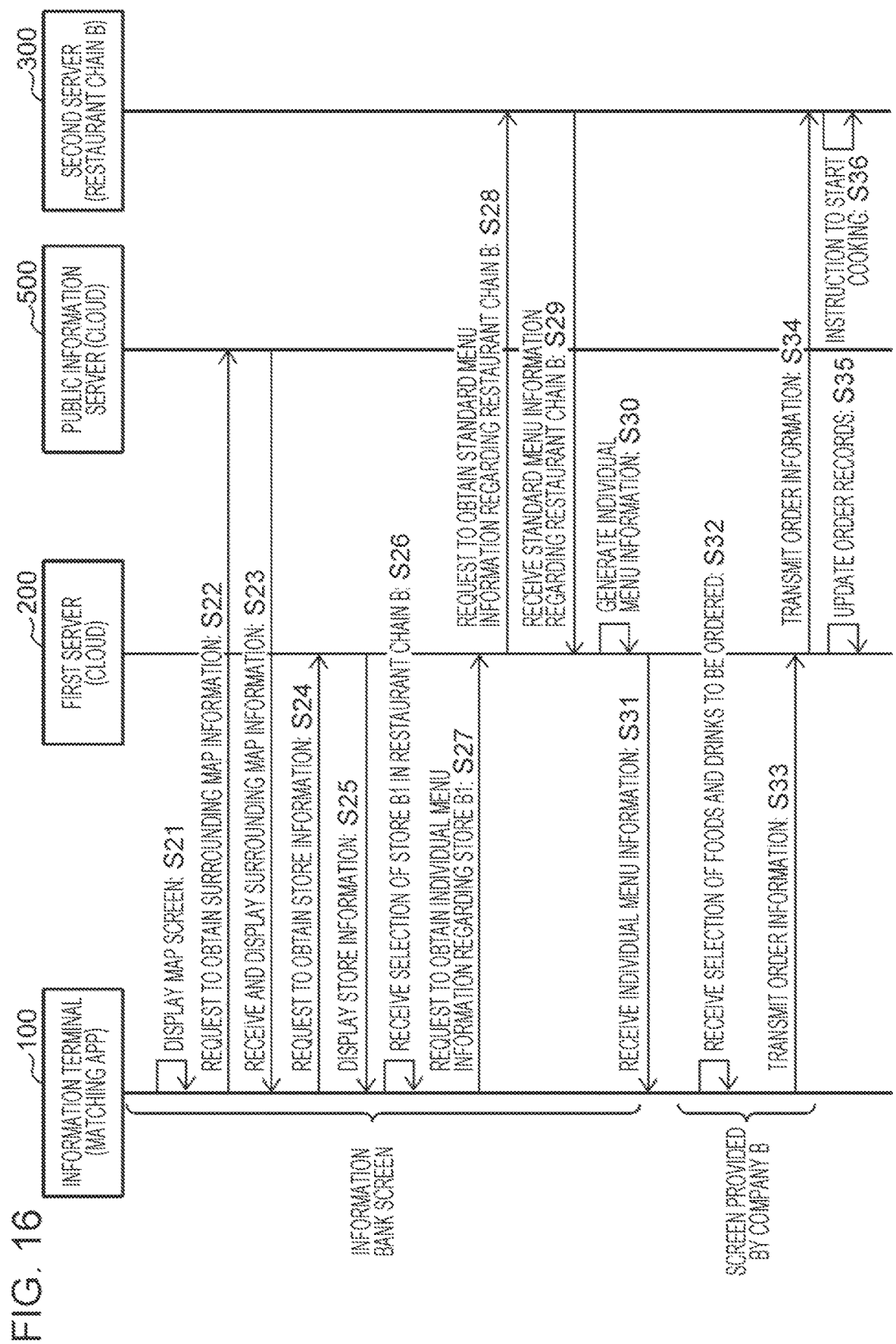
FIG. 16 is a sequence diagram illustrating an example of a process performed by the information provision system when the user's order for foods and drinks is received in consideration of whether a store that the user is visiting belongs to a restaurant chain that the user uses for a first time.

FIG. 16 is a sequence diagram illustrating an example of a process performed by the information provision system when the user's order for foods and drinks is received in consideration of whether a store that the user is visiting belongs to a restaurant chain that the user uses for a first time.

Steps S21 to S25 are the same as steps S1 to S5 illustrated in FIG. 15, respectively. In step S26, the matching app receives, from the user, an instruction to select store B1 in restaurant chain B among the stores displayed in the map screen G4.

In step S27, the matching app transmits, to the first server 200, a request to obtain individual menu information regarding store B1. The request includes the store ID of store B1, connection information regarding store B1, and the user ID of the information terminal 100.

Upon receiving the request, the first server 200 transmits, to a second server 300 for restaurant chain B, a request to obtain standard menu information regarding restaurant chain B to which store B1 belongs (step S28).

Upon receiving the request, the second server 300 for restaurant chain B transmits the standard menu information regarding store B1 to the first server 200. The first server 200 receives the standard menu information regarding restaurant chain B (step S29). The standard menu information regarding restaurant chain B transmitted here may be menu information common to stores in restaurant chain B or menu information partly different between the stores in restaurant chain B.

Upon receiving the standard menu information regarding restaurant chain B, the first server 200 generates individual menu information regarding store B1 for the user on the basis of order records of the user (step S30). More specifically, if the order records of the user at restaurant chain B do not satisfy a reference condition C1, which will be described later, the first server 200 generates individual menu information regarding store B1 using order records of the user about foods and drinks that are the same as or similar to foods and drinks served at store B1 in restaurant chain B. If the order records of the user at restaurant chain B satisfy the reference condition C1, on the other hand, the first server 200 generates individual menu information regarding store B1 for the user using order records of the user at restaurant chain B. Details of step S30 will be described later with reference to a flowchart of FIG. 17.

The first server 200 transmits, to the information terminal 100 (matching app), the generated individual menu information regarding store B1, and the matching app receives the individual menu information (step S31).

In the steps up to step S31, various screens displayed on the information terminal 100 designed in a style defined by the manager (information bank) of the first server 200 are used. In step S32 and later steps, however, various screens displayed on the information terminal 100 are designed in a style defined by restaurant chain B.

In step S32, the matching app displays the individual menu screen G5 or G6 indicating the received individual menu information regarding store B1 and receives, from the user, an instruction to select foods and drinks to be ordered.

Steps S33 to S36 are the same as steps S12 to S16 illustrated in FIG. 15, respectively, except that foods and drinks are ordered at store B1, not store A1, in steps S33 to S36.

Figure 17:
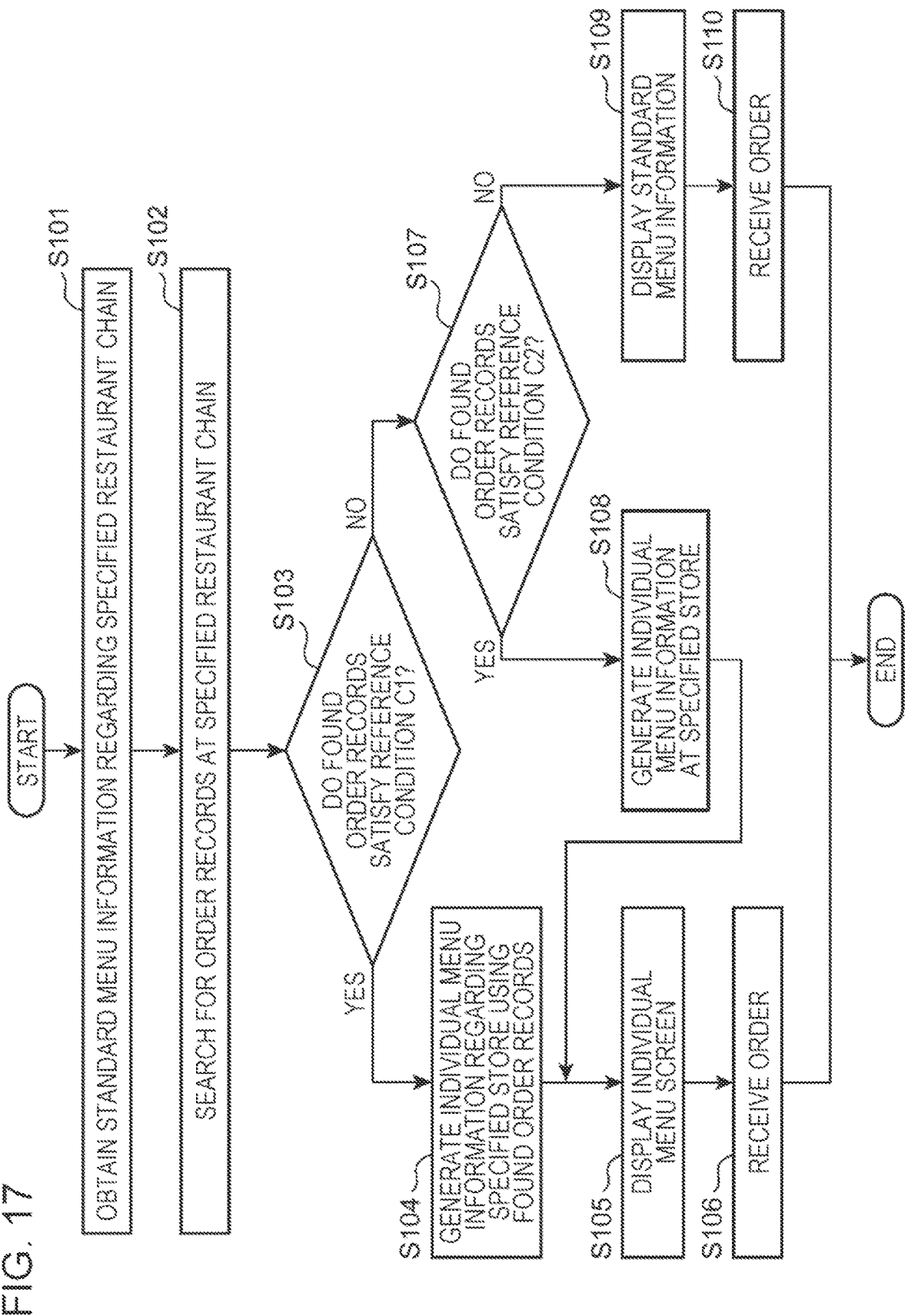
FIG. 17 is a diagram illustrating an example of a process at a time when step S30 in the sequence diagram of FIG. 16 is focused upon.

FIG. 17 is a diagram illustrating an example of a process performed by the information provision system at a time when step S30 in the sequence diagram of FIG. 16 is focused upon.

In step S101, the first server 200 obtains, from the second server 300, standard menu information regarding a specified restaurant chain. This step corresponds to step S29 illustrated in FIG. 16. The specified restaurant chain is a restaurant chain to which a store selected by the user on the map screen G4 belongs.

FIG. 13 is a diagram illustrating an example of the data configuration of standard menu information D1. In the standard menu information D1, "name", "price", and "time limit" are associated with one another for each of one or more foods and drinks. "Name" indicates a name of a food or a drink, such as "blended coffee" or "American coffee". "Price" indicates a price of a food or a drink. "Time limit" indicates whether a food or a drink is an item on sale for a limited time. "Yes" indicates an item on sale for a limited time, and "no" indicates a constantly available item. For example, "special Mont Blanc white caffe latte" is a drink served in a particular period, and "time limit" is "yes".

FIG. 17 will be referred to again. In step S102, the first server 200 searches order records of the user stored in the memory 203 for ones at the specified restaurant chain.

In step S103, the first server 200 determines whether the found order records satisfy the reference condition C1. The reference condition C1 may include at least one of following (a) to (d) in a period of time set by the company that manages the first server 200, the company that develops the matching app, the company that distributes the matching app, a company that provides the service (here, restaurant chain B), or the user. The period of time may be, for example, a limited period such as past three years, past two years, or a past one year or an unlimited period.

(a) The number of orders for foods and drinks at the specified restaurant chain is larger than or equal to a threshold Ta (b) The number of days when the user has ordered foods and drinks at the specified restaurant chain (the number of times that the user has visited the specified restaurant chain) is larger than or equal to a threshold Tb (c) The number of foods and drinks (the number of dishes) ordered at the specified restaurant chain is larger than or equal to a threshold Tc (d) The total amount of money paid for foods and drinks ordered at the specified restaurant chain (order amount) is larger than or equal to a threshold Td For each of the thresholds Ta to Td, for example, a predetermined value with which the user is considered to visit the specified restaurant chain frequently is used. Alternatively, a predetermined value with which the user is considered to be visiting the specified restaurant chain essentially for a first time may be used for each of the thresholds Ta to Td.

The period of time is provided as a condition in order to take into consideration a possibility that the user has not visited the specified restaurant chain for a long time and the user's taste has changed during that time or that stores in the specified restaurant chain have updated a menu. The user's taste might change, for example, when the user becomes more conscious about health.

If the found order records satisfy the reference condition C1 (YES in step S103), the first server 200 generates individual menu information regarding a specified store for the user using the found order records as priority indices (step S104). The specified store is a store selected by the user on the map screen G4. If the specified store is store B1 and the user frequently visits store B1 or any of the other stores in restaurant chain B, for example, a result of step S103 becomes YES. In this case, for example, the first server 200 may increase, on the basis of the number of orders based on the found order records, priority of foods and drinks ordered more. In addition, the first server 200 may rank foods and drinks in descending order of a possibility of being ordered while taking into consideration surrounding conditions of the user at a time of ordering. For example, appeal priority of foods and drinks in an individual menu may be determined on the basis of the number of orders under surrounding conditions ("day", "season", "temperature", "humidity", "weather", "place", "store", "biological information regarding user", and/or "amount of activity of user") similar to ones of current ordering. In this case, foods and drinks are not recommended regardless of conditions just because the number of orders for the foods and the drinks is the largest. The first server 200 may then generate individual menu information by rearranging menu items in the standard menu information regarding restaurant chain B such that the user can easily order prioritized foods and drinks. The individual menu information is transmitted to the information terminal 100.

FIG. 12 is a diagram illustrating an example of the data configuration of an order record database D2 storing order records. FIG. 12 illustrates an order record database D2 for the user who has specified a store. In each of order records of the order record database D2, for example, details of the user's order in each visit to a store are stored. In the order record database D2, "order time information", "store ID", "store name", and "ordered item names" are associated with one another. The order record database D2 is encrypted and managed while being split into "userID_FoodHistory_tjson" to "userID_FoodHistory_N.json" files illustrated in FIG. 18, which will be referred to later.

"Order time information" indicates a time at which the user has ordered foods and drinks. "Store ID" is identification information regarding a store that the user has visited. "Store name" indicates a name of a store that the user has visited. Here, "store name" also includes a name of a restaurant chain to which the store belongs. "Ordered item names" indicate names of foods and drinks ordered by the user. In a first order record, for example, information indicating that the user has ordered cappuccino and ice cream at Kadoma store in restaurant chain A at 13:15:45 on Jan. 3, 2020.

Although the above-described surrounding conditions are not illustrated, information regarding surrounding conditions may also be stored in order records. "Day" indicates a day of ordering, "season" indicates a season of ordering, "temperature" indicates a temperature around the user at a time of ordering, "humidity" indicates a humidity around the user at a time of ordering, "weather" indicates weather around the user at a time of ordering (sunny, rainy, cloudy, etc.), "place" is information (an address, GPS information, etc.) indicating a place of ordering, "store" is information for identifying a store at which the user has ordered foods and drinks, "biological information regarding user" is biological information (blood pressure, heart rate, etc.) regarding the user at a time of ordering, and "amount of activity of user" is activity information (the number of steps, calories consumed, etc.) regarding the user.

If the specified restaurant chain is restaurant chain B, the first server 200 may refer to the order record database D2 and collect the number of orders for each of foods and drinks included in the standard menu information D1 regarding restaurant chain B. The first server 200 may then rank the foods and the drinks included in the standard menu information D1 from a result of the collection and generate individual menu information.

In step S105, the information terminal 100 displays an individual menu screen indicating the individual menu information. In step S106, the information terminal 100 receives, from the user, an instruction to select foods and drinks to be ordered.

If the found order records do not satisfy the reference condition C1 in step S103 (NO in step S103), the first server 200 determines whether the order records of the user satisfy a reference condition C2 (step S107).

The reference condition C2 may include at least one of following (e), (f), and (g) in a period of time set by the company that manages the first server 200, the company that develops the matching app, the company that distributes the matching app, the company that provides the service (here, restaurant chain B), or the user. The period of time may be a limited period such as past three years, past two years, or past one year or an unlimited period.

(e) The sum of count values is larger than or equal to a threshold Te (f) The number of foods and drinks whose count values are larger than or equal to a threshold Tf is larger than or equal to a certain value (g) The sum of order amounts is larger than or equal to a threshold Tg A count value indicates the number of times that each of foods and drinks included in standard menu information regarding a specified restaurant chain appears in the "ordered item names" field of the order record database D2. A count value is measured through text matching in which the number of times that a character string to be searched for appears in a target text. If a character string "cappuccino" included in standard menu information appears 29 times in the "ordered item names" field of the order record database D2 within a set period of time (e.g., three years), for example, a count value of "cappuccino" is 29. When standard menu information separately includes "dan dan noodles" and "Chinese dumplings" and the "ordered item names" field of the order record database D2 includes "dan dan noodles & Chinese dumplings set", for example, count values of "dan dan noodles" and "Chinese dumplings" may each be increased by 1.

The sum of count values is the sum of count values of foods and drinks for the user. In the example illustrated in FIG. 14, the sum of count values of foods and drinks for the user is 2+29+11+3=45 with respect to illustrated items, namely from "blended coffee" to "special Mont Blanc white caffe latte".

A count value of each of foods and drinks included in a standard menu increases if the "ordered item names" field of the order record database D2 includes a food or a drink whose character string is the same as or similar to that of the food or the drink included in the standard menu. "Blended coffee" and "original blended coffee", for example, are determined to be similar to each other because one character string includes another. The sum of count values is the sum of count values of foods and drinks.

If the threshold Tf is 10, foods and drinks whose count values are larger than or equal to the threshold Tf are "cappuccino" and "caffe mocha" in the example of the order record database D2. In this case, if the certain value in the condition (f) is 2, it is determined that the order records of the user satisfy the condition (f).

If the order records satisfy the reference condition C2 (YES in step S107), the first server 200 generates individual menu information regarding the specified store using the order records of the user (step S108). In this case, the first server 200 may generate individual menu information such that it becomes easier for the user to order foods and drinks whose count values, that is, number of orders, are larger. After step S108, the process proceeds to step S105, and step S105 and a later step is performed.

The sum of order amounts is the sum of prices of foods and drinks multiplied by the number of orders. The sum of order amounts are 2*350+29*350+11*350+3150=15,150 yen with respect to the items illustrated in FIGS. 13 and 14.

FIG. 14 is a table illustrating the number of orders placed by a certain user for foods and drinks included in standard menu information. In the table, "total number of orders" indicates the number of orders for each of the foods and the drinks at all restaurant chains including a specified restaurant chain. "Number of orders at specified restaurant chain" indicates the number of orders placed by the user for each of the foods and drinks at a restaurant chain to which a store selected by the user on the map screen G4 belongs.

Because the number of orders at the specified restaurant chain is zero for every one of the foods and the drinks, it can be seen that the user has never visited the restaurant chain. It is therefore difficult to generate individual menu information that suits the user's taste on the basis of order records at the restaurant chain. The number of orders for "cappuccino" and "caffe mocha", however, is large in the "total number of orders" field, and the user's taste is evident.

The first server 200, therefore, generates individual menu information while referring to "total number of orders". As a result, the first server 200 can generate individual menu information that suits the user's taste. In the example illustrated in FIG. 14, "total number of orders" for "cappuccino" and "caffe mocha" is larger than that of any other food or drink. Even if the user uses a specified restaurant for a first time, therefore, these drinks are displayed in an initial screen of an individual menu screen in such a manner that the user can easily order the drinks. A food or a drink whose "total number of orders" is small, such as "American coffee", may be removed from the initial screen of the individual menu screen. Alternatively, when tile objects 701 indicating foods and drinks whose "total number of orders" is large can be displayed in the initial screen of the individual menu screen, "American coffee" may also be displayed. In this case, a tile object 701 indicating a food or a drink whose "total number of orders" is small, such as "American coffee", may be displayed smaller than tiles objects 701 indicating "cappuccino" and "caffe mocha".

If the order records satisfy the reference condition C2, the count value of each of the foods and the drinks may be calculated while excluding the number of orders at the specified restaurant chain from "total number of orders" illustrated in FIG. 14. Alternatively, if the order records satisfy the reference condition C2, the count value of each of the foods and the drinks may be calculated while weighting the number of orders at the specified restaurant chain and the number of orders at other restaurant chains differently (e.g., weighting the number of orders at the specified restaurant chain more heavily than the number of orders at the other restaurant chains) in "total number of orders" illustrated in FIG. 14. Alternatively, if the order records satisfy the reference condition C2, the count value of each of the foods and the drinks may be calculated using "total number of orders" at certain one or more restaurant chains other than the specified restaurant chain in "total number of orders" illustrated in FIG. 14. The certain one or more restaurant chains are restaurant chains that the user frequently visits.

FIG. 17 will be referred to again. In step S107, if the order records of the user do not satisfy the reference condition C2 (NO in step S107), the first server 200 displays, on the information terminal 100, a standard menu screen for the restaurant chain to which the store selected by the user on the map screen G4 belongs (step S109).

By providing branching at step S107, generation of individual menu information can be prevented, for example, if the number of order records of the user stored in the order record database D2 is small and it is difficult to estimate the user's taste from the order record database D2. In step S110, the information terminal 100 receives, from the user who has viewed the standard menu screen, an instruction to select foods and drinks to be ordered.

Example of Information Processing when User Orders Using Individual Menu

Next, an example of information processing when the user orders foods and drinks using an individual menu screen will be described. When an interface for communicating information and a data structure to be handled are unique to a restaurant chain or a store, various pieces of data handled in the information provision system might be available at store A1 in restaurant chain A but might be unavailable at restaurant chain B, or might be unavailable at both other stores in restaurant chain A and restaurant chain B. In order to avoid such situations, a general-purpose solution for enabling many users to order foods and drinks using individual menus at many restaurants will be described.

Figure 18:
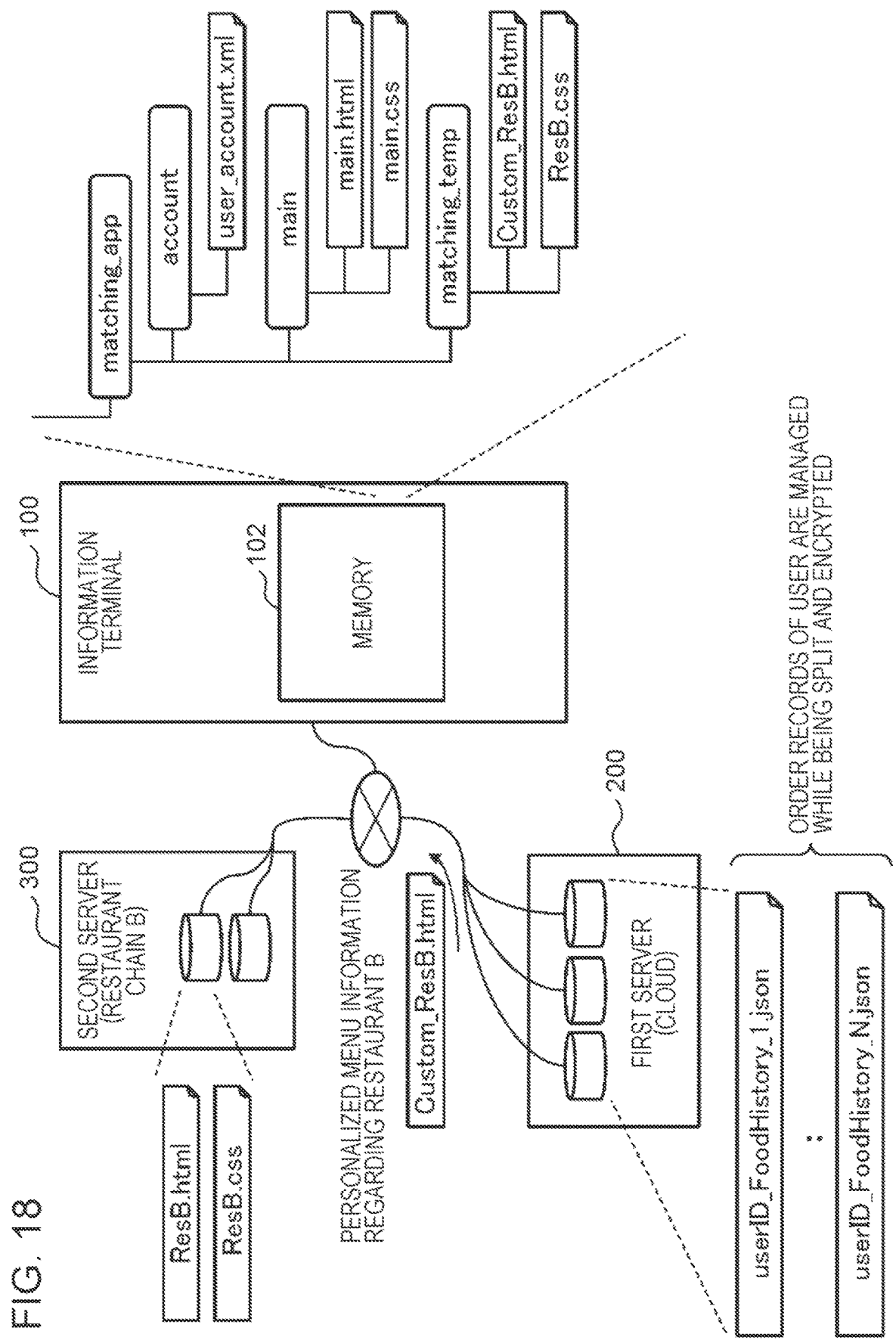
FIG. 18 is a diagram illustrating an example of a specific mode for implementing the information provision system according to the first embodiment.

FIG. 18 is a diagram illustrating an example of a specific mode for implementing the information provision system according to the present embodiment. The memory 102 of the information terminal 100 includes a "matching_app" directory, which is a location storing files necessary to execute the matching app. There are an "account" directory, a "main" directory, and a "matching_temp" directory under the "matching_app" directory. The "account" directory stores information necessary for user accounts and/or user authentication. The "main" directory stores information necessary for the matching app to achieve basic functions including drawing of the home screen. The "matching_temp" directory temporarily stores information necessary for matching.

The "account" directory stores a "user_account.xml" file containing information necessary for accounts and/or user authentication. In the "user_account.xml" file, unique account names (e.g., user IDs specified by users) and authentication information (e.g., passwords, fingerprint feature values, and/or face feature values) are encrypted and recorded as information for identifying the users.

Each of the account names is not limited to a user ID specified by a user and may be information with which the user who uses the matching app can be uniquely identified. For example, a serial code unique to each set of the matching app may be employed, the serial code being embedded in a program of the matching app or distributed along with the matching app. The serial code unique to each set of the matching app is a serial code uniquely given to an information terminal 100 on which the matching app is installed. Alternatively, each of the account names may be a unique account name generated by the matching app on the basis of random numbers when the matching app is activated for a first time or the account name is registered. In this case, the matching app may automatically generate an account name while confirming, with the first server 200, that the account name is not one of existing account names that have been registered.

When character string information meaningless to humans is set as an account name, personal information of increased secrecy can be communicated.

The "main" directory stores a "main.html" file containing content information necessary to achieve the basic functions of the matching app and a "main.css" file containing a style (e.g., a user interface (UI) design) for displaying screens.

The second server 300 for restaurant chain B stores a "ResB.html" file containing content information to reply with and a "ResB.css" file containing a style (e.g., a UI design) for displaying screens for the content information. For example, the "ResB.html" file may include the standard menu information D1 illustrated in FIG. 13. Alternatively, an external file referred to with the "ResB.html" file may store the standard menu information D1.

An enormous amount of a wide variety of personal information regarding the user is accumulated in the first server 200 while being split and encrypted. For example, the order record database D2 for the user used in the present disclosure may be stored in physically different storage devices in the first server 200 as N JavaScript object notation (JSON)-format files, namely a "userID_FoodHistory_1.json" file, a "userID_FoodHistory_2.json", . . . , and a "userID_FoodHistory_N.json" file. In each of the N files, "userID" at a beginning of a filename is identification information for identifying the user and "FoodHistory" is identification information for identifying the order record database D2 described with reference to FIG. 12. A number at an end of the filename is an identification number of the file obtained as a result of the splitting.

If the first server 200 can receive a request for order records of the user along with an appropriate permission (e.g., access permission information), the first server 200 can correctly restore data from the N files, encrypt the data by converting the data into a certain description format (.json), and transmit the data to the information terminal 100.

Figure 19:
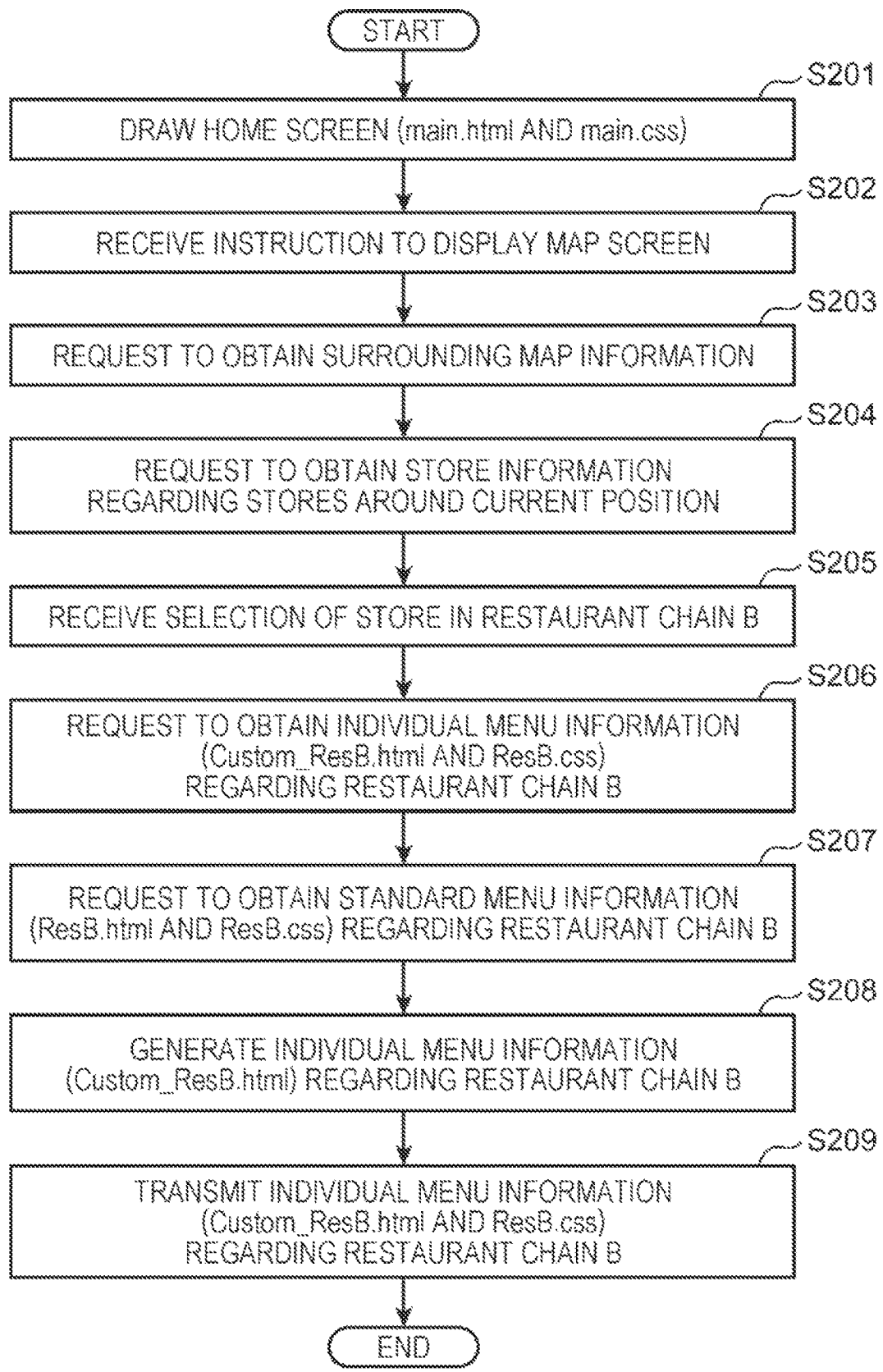
FIG. 19 is a flowchart illustrating an example of a process performed by the matching app on files until an image of an individual menu is displayed after the matching app is activated.

How the matching app handles files when controlling screens using a hypertext markup language (HTML) will be described with reference to a flowchart of FIG. 19. FIG. 19 is a flowchart illustrating an example of a process performed by the matching app on the files until an image of an individual menu is displayed after the matching app is activated.

In step S201, the matching app is activated and draws the home screen. The matching app draws the home screen using the "main.html" file and the "main.css" file in the "main" directory immediately after the activation. As a result, the home screen G3 illustrated in FIG. 5 is drawn.

In step S202, the matching app receives, from the user who is viewing the home screen G3, an instruction to display the map screen G4.

In step S203, the matching app transmits, to the public information server 500, a request to obtain surrounding map information at a current position and displays the map screen G4 indicating the surrounding map information.

In step S204, the matching app transmits, to the first server 200, a request to obtain store information regarding stores in an area indicated by the surrounding map information and displays the store information in the map screen G4. As a result, the icon 3210 and the like indicating the stores are displayed.

In step S205, the matching app receives, from the user, an instruction to select store B1 in restaurant chain B.

In step S206, the matching app transmits, to the first server 200, a request to obtain individual menu information regarding restaurant chain B.

In step S207, the first server 200 transmits, to the second server 300 for restaurant chain B, a request to obtain standard menu information (ResB.html and ResB.css) regarding restaurant chain B.

In step S208, the first server 200 generates individual menu information regarding restaurant chain B from the order records of the user. The generated individual menu information is newly stored under the "matching_temp" directory as a "Custom_ResB.html" file.

In step S209, the first server 200 transmits the individual menu information regarding restaurant chain B to the matching app.

Various screens are thus drawn using HTML/cascading style sheets (CSS) files. When a single matching app presents, from among products or services provided by a large number of unspecified business operators, products or services that suit an enormous amount of a wide variety of personal information regarding a user, therefore, information expected by the business operators can be displayed in styles (e.g., UI designs) expected by the business operators.

When a user who has finished ordering foods and drinks using an individual menu returns to the home screen of the matching app, or when a certain period of time has elapsed since a user finished ordering foods and drinks using an individual menu, files temporarily stored in the "matching_temp" directory may all be removed for the sake of safety.

The above description is just an example, and those skilled in the art may implement various applications of the present disclosure.

(1) When the first server 200 obtains order information for store B1 in restaurant chain B selected by the user on the map screen G4, the first server 200 may monitor the current position of the information terminal 100. When a distance between the information terminal 100 and store B1 becomes smaller than or equal to a certain value, the first server 200 may transmit the order information to the second server 300 of restaurant chain B. As a result, store B1 can promptly provide foods and drinks for the user when the user arrives at store B1.

(2) In each of the above embodiments, each of the components may be achieved by dedicated hardware or by executing a software program corresponding to the component. Each of the components may be achieved by reading and executing a software program stored in a storage medium such as a hard disk or a semiconductor memory using a program execution unit such as a CPU or a processor, instead.

(3) Count values need not be calculated for foods and drinks that are included in the standard menu information D1 illustrated in FIG. 13 and for which time limits are provided. That is, count values may be calculated only for foods and drinks whose "time limit" is No in standard menu information, and individual menu information may be generated on the basis of a result of the calculation.

(4) In the present disclosure, a case where individual menu information is generated at a store in a second restaurant chain at which the user has never or hardly ever placed an order using personal information such as order records at stores in a first restaurant chain at which the user has placed orders and a result of comparison between names of foods and drinks served at stores in the second restaurant chain and names of foods and drinks served at the stores in the first restaurant chain has been described as an example. Information used in combination with personal information in order for the first server 200 to generate individual menu information, however, is not limited to the above example.

For example, the first server 200 may generate individual menu information using statistical information estimated from big data including purchase records of users who have placed orders at both stores in the first restaurant chain and the stores in the second restaurant chain, instead. In this case, if it is determined, from personal information regarding a user who is using a service, that the user has frequently ordered an item A at the stores in the first restaurant chain, for example, the first server 200 generates individual menu information in which an item X takes priority in display, that is, the item X is displayed at a position of high priority, for example, on the basis of statistical information obtained by analyzing big data, the statistical information indicating "users who order the item A at the stores in the first restaurant chain frequently orders the item X at the stores in the second restaurant chain".

Although information obtained by analyzing big data is called "statistical information" above, a term used is not limited to this. For example, the information may be called "correlation information indicating a correlation between an item served at the stores in the first restaurant chain and an item served at the stores in the second restaurant chain" or simply called "information generated using big data". Information obtained from other users and that is used as big data may be, for example, used for an analysis or the like after being converted into anonymous information with which the users are not identified. Alternatively, when generating the statistical information, the first server 200 may anonymize personal information associated with a user who is using a service used to generate an individual menu.

(5) In the present disclosure, an example has been described where the first server 200 generates individual menu information in which foods and drinks are arranged in order according to taste information regarding the user estimated from purchase records of the user or the like. In the following description, a method in which the first server 200 controls or specifies, through individual menu information, order of foods and drinks displayed on a terminal apparatus in an individual menu will be described while taking some examples. That is, a method for providing information in which the first server 200 generates, on the basis of taste information regarding a user including order records at a first restaurant and menu information regarding a second restaurant, individual menu information for arranging, on a display screen of a terminal apparatus, menu items included in the menu information regarding the second restaurant in order according to the taste information, transmits the individual menu information to the terminal apparatus, and displays menu information regarding the menu items arranged in the order on the display screen of the terminal apparatus will be described with reference to some examples. A method used by the first server 200 to control or specify order of foods and drinks displayed in an individual menu and that can be implemented in the above embodiments is not limited to the above example. That is, the first server 200 may use any method insofar as order of foods and drinks displayed in an individual menu can be changed in accordance with taste information estimated from personal information such as order records.

In a first example, when generating individual menu information, the first server 200 stores foods and drinks, which are menu items, in the individual menu information in order in which the foods and the drinks are to be displayed.

In a second example, when generating individual menu information, the first server 200 directly specifies a display position in a screen for each of foods and drinks to be displayed in an individual menu.

In a third example, the first server 200 stores each of foods and drinks to be displayed in an individual menu in individual menu information while associating the food or the drink with a position in order of display. In this case, an app or a browser on the terminal apparatus that has received the individual menu information may determine, on the basis of a certain display screen generation rule, for example, the number of foods and drinks, display sizes of the foods and the drinks corresponding to the positions in the order of display, display positions of the foods and the drinks corresponding to the positions in the order of display, and the like in accordance with the size of an area in which the individual menu is to be displayed or the display size of a font specified by the user and generate a display screen for the individual menu by disposing objects indicating the foods and the drinks in accordance with the positions in the order of display included in the individual menu information.

In a fourth example, the first server 200 may store, in the individual menu information for each of the foods and the drinks, one or more parameters that have been generated on the basis of personal information regarding the user and that are available in determining the position of the food or the drink in the order of display instead of directly storing the position of the food or the drink in the order of display in the individual menu information. Upon receiving the individual menu information, the app or the browser on the terminal apparatus calculates the position of the food or the drink in the order of display from the one or more parameters in accordance with a certain display position calculation rule or a display position calculation rule specified by the user from among more than one candidate. With this configuration, the app or the browser on the terminal apparatus does not simply display a display screen for an individual menu in accordance with generated individual menu information but can adjust a method for displaying an individual menu or positions of foods and drinks in order of display in accordance with a type of terminal apparatus used by the user or settings made by the user. The service, therefore, can be provided more flexibly.

Although the information provision system and the method for providing information according to one or more aspects have been described on the basis of embodiments, the present disclosure is not limited to the embodiments. The scope of the present disclosure may also include modes obtained by modifying the above embodiments in ways conceivable by those skilled in the art and modes constructed by combining together components from different embodiments, insofar as the spirit of the present disclosure is not deviated from.

With an example of the method for providing information in the present disclosure, the user can efficiently order foods and drinks. The method for providing information, therefore, is effective as a technique used in a restaurant industry, where the user is served with foods and drinks.

What is claimed is:

1. A method for providing information in an information management system that manages taste information regarding a user including an order record at a first restaurant and that associates the taste information with identification information for identifying the user, the method comprising:
obtaining, from a terminal apparatus, the identification information and a store identifier indicating a second restaurant in a chain different from a chain to which the first restaurant belongs, the store identifier being selected on the terminal apparatus;
arranging, on a basis of the taste information associated with the identification information and menu information regarding the second restaurant indicated by the store identifier, using order records of the user about menu items of the first restaurant that are the same as or similar to menu items included in the menu information, the menu items included in the menu information in order according to the taste information based on a position of priority, the menu information being obtained, over a network, from a server relating to the second restaurant indicated by the store identifier; and
transmitting menu information regarding the menu items arranged in the order to the terminal apparatus to display the menu information regarding the menu items arranged in the order on a display screen of the terminal apparatus.

2. The method according to claim 1,
wherein the second restaurant includes a coffee shop in a chain different from the chain to which the first restaurant belongs.

3. The method according to claim 1,
wherein the second restaurant includes a hamburger shop in a chain different from the chain to which the first restaurant belongs.

4. The method according to claim 1, further comprising:
obtaining positional information regarding the terminal apparatus of the user; and
providing, on a basis of the positional information, the terminal apparatus with restaurant information indicating one or more restaurants in an area including a position indicated by the positional information,
wherein the store identifier is selected on the terminal apparatus on a basis of the restaurant information.

5. The method according to claim 4,
wherein the positional information regarding the terminal apparatus of the user is obtained using a global positioning system.

6. The method according to claim 1,
wherein, the information management system manages an order record at the second restaurant and associates the order record at the second restaurant with identification information for identifying the user, and
wherein, when there is no order record of the user at the second restaurant in the information management system, the menu items included in the menu information regarding the second restaurant are arranged in the order according to the taste information associated with the identification information on a basis of the taste information and the menu information regarding the second restaurant.

7. The method according to claim 6,
wherein, when there is an order record of the user at the second restaurant in the information management system, the menu items included in the menu information regarding the second restaurant are arranged in order according to the order record at the second restaurant on a basis of the order record at the second restaurant and the menu information regarding the second restaurant.

8. The method according to claim 1,
wherein, the information management system manages an order record at the second restaurant and associates the order record at the second restaurant with identification information for identifying the user, and
wherein, when a number of order records of the user at the second restaurant is smaller than a certain value in the information management system, the menu items included in the menu information regarding the second restaurant are arranged in the order according to the taste information associated with the identification information on a basis of the taste information and the menu information regarding the second restaurant.

9. The method according to claim 8,
wherein, when the number of order records of the user at the second restaurant is larger than or equal to the certain value in the information management system, the menu items included in the menu information regarding the second restaurant are arranged in order according to the order record at the second restaurant on a basis of the order record at the second restaurant and the menu information regarding the second restaurant.

10. The method according to claim 1,
wherein, the information management system manages an order record at the second restaurant and associates the order record at the second restaurant with identification information for identifying the user, and
wherein, when a latest order record of the user at the second restaurant precedes a certain period of time in the information management system, the menu items included in the menu information regarding the second restaurant are arranged in the order according to the taste information associated with the identification information on a basis of the taste information and the menu information regarding the second restaurant.

11. The method according to claim 10,
wherein, when the latest order record of the user at the second restaurant is within the certain period of time in the information management system, the menu items included in the menu information regarding the second restaurant are arranged in order according to the order record at the second restaurant on a basis of the order record at the second restaurant and the menu information regarding the second restaurant.

12. A method for providing information in an information management system that manages taste information regarding a user including an order record at a first restaurant and that associates the taste information with identification information for identifying the user, the method comprising:
- obtaining positional information regarding a terminal apparatus of the user;
- providing, on a basis of the positional information, the terminal apparatus with restaurant information indicating one or more restaurants in an area including a position indicated by the positional information;
- obtaining, from the terminal apparatus, the identification information and a store identifier indicating, among the one or more restaurants, a second restaurant in a chain different from a chain to which the first restaurant belongs, the store identifier being selected on the terminal apparatus;
- arranging, on a basis of the taste information associated with the identification information and menu information regarding the second restaurant indicated by the store identifier, using order records of the user about menu items of the first restaurant that are the same as or similar to menu items included in the menu information, the menu items included in the menu information in order according to the taste information based on a position of priority, the menu information being obtained, over a network, from a server relating to the second restaurant indicated by the store identifier; and
- transmitting menu information regarding the menu items arranged in the order to the terminal apparatus to display the menu information regarding the menu items arranged in the order on a display screen of the terminal apparatus.

13. The method according to claim 1,
wherein, the information management system manages an order at the second restaurant and associates the order at the second restaurant with identification information for identifying the user, and
wherein, when, in the information management system, a number of orders at the second restaurant within a set period of time is determined smaller than or equal to a certain value, the menu items included in the menu information regarding the second restaurant are arranged in the order according to the taste information on a basis of the taste information and the menu information.

14. The method according to claim 12,
wherein, the information management system manages an order at the second restaurant and associates the order at the second restaurant with identification information for identifying the user, and
wherein, when, in the information management system, a number of orders at the second restaurant within a set period of time is determined smaller than or equal to a certain value, the menu items included in the menu information regarding the second restaurant are arranged in the order according to the taste information on a basis of the taste information and the menu information.

15. The method according to claim 1,
wherein, in the information management system, the order record at the first restaurant and a store identifier indicating the first restaurant are stored and are associated with each other.

16. The method according to claim 12,
wherein, in the information management system, the order record at the first restaurant and a store identifier indicating the first restaurant are stored and are associated with each other.

* * * * *